(12) United States Patent
Frechet et al.

(10) Patent No.: US 8,137,700 B2
(45) Date of Patent: Mar. 20, 2012

(54) MAIN CHAIN ACID-DEGRADABLE POLYMERS FOR THE DELIVERY OF BIOACTIVE MATERIALS

(75) Inventors: Jean M. J. Frechet, Oakland, CA (US); Stephany M. Standley, Evanston, IL (US); Rachna Jain, Milpitas, CA (US); Cameron C. Lee, Cambridge, MA (US)

(73) Assignee: U.S. Department of Energy, Washington, DC (US)

( * ) Notice: Subject to any disclaimer, the term of this patent is extended or adjusted under 35 U.S.C. 154(b) by 400 days.

(21) Appl. No.: 12/299,506

(22) PCT Filed: May 4, 2007

(86) PCT No.: PCT/US2007/068284
§ 371 (c)(1),
(2), (4) Date: Apr. 3, 2009

(87) PCT Pub. No.: WO2007/131193
PCT Pub. Date: Nov. 15, 2007

(65) Prior Publication Data
US 2009/0220615 A1    Sep. 3, 2009

Related U.S. Application Data

(63) Continuation-in-part of application No. 11/388,924, filed on Mar. 28, 2006.

(60) Provisional application No. 60/798,177, filed on May 5, 2006.

(51) Int. Cl.
*A61K 9/50* (2006.01)
*A61K 38/00* (2006.01)
*A01N 61/00* (2006.01)
*C08G 73/00* (2006.01)
*C08G 65/34* (2006.01)
*C08G 67/02* (2006.01)

(52) U.S. Cl. ............ 424/501; 514/1; 514/1.1; 528/422; 528/425; 528/367; 528/392

(58) Field of Classification Search .................. None
See application file for complete search history.

(56) References Cited

U.S. PATENT DOCUMENTS

| 4,036,882 | A | * | 7/1977 | Bertozzi et al. | ............. | 564/474 |
| 5,191,015 | A | * | 3/1993 | Sheppard et al. | ............ | 525/54.1 |
| 7,056,901 | B2 | * | 6/2006 | Frechet et al. | ................... | 514/54 |
| 7,683,041 | B2 | * | 3/2010 | Frechet et al. | ................... | 514/59 |

OTHER PUBLICATIONS

Kwon et al. (Molecular Pharmaceutics, vol. 2, No. 1, p. 83-89, Published Jan. 7, 2005).*
Murthy et al. (Journal of the American Chemical Society, 124, p. 12398-12399, Published Oct. 4, 2002).*
Standley et al. (Bioconjugate Chemistry, 15, Published 2004, p. 1281-1288).*
Kwon et al. (Journal of Controlled Release, 105, Published 2005, p. 199-212).*

* cited by examiner

*Primary Examiner* — Richard Schnizer
*Assistant Examiner* — Alma Pipic
(74) *Attorney, Agent, or Firm* — Mark C. Lang; Brian J. Lally; John T. Lucas

(57) ABSTRACT

Novel main chain acid degradable polymer backbones and drug delivery systems comprised of materials capable of delivering bioactive materials to cells for use as vaccines or other therapeutic agents are described. The polymers are synthesized using monomers that contain acid-degradable linkages cleavable under mild acidic conditions. The main chain of the resulting polymers readily degrade into many small molecules at low pH, but remain relatively stable and intact at physiological pH. The new materials have the common characteristic of being able to degrade by acid hydrolysis under conditions commonly found within the endosomal or lysosomal compartments of cells thereby releasing their payload within the cell. The materials can also be used for the delivery of therapeutics to the acidic regions of tumors and other sites of inflammation.

22 Claims, 13 Drawing Sheets

FIG. 12

| Polymer | Degradation Product |
|---|---|
| 17 | HO-CH₂CH₂-NH-C(=O)-NH-(CH₂)₆-NH-C(=O)-NH-CH₂CH₂-OH |
| 18 | HO-CH₂CH₂-NH-C(=O)-NH-(methylphenyl)-NH-C(=O)-NH-CH₂CH₂-OH |
| 19 | HO-CH₂CH₂-NH-C(=O)-NH-CH₂CH₂-O-CH₂CH₂-O-CH₂CH₂-NH-C(=O)-NH-CH₂CH₂-OH |
| 20 | HO-CH₂CH₂-NH-C(=O)-O-(CH₂)₆-O-C(=O)-NH-CH₂CH₂-OH |
| 21 | HO-CH₂CH₂-NH-C(=O)-O-CH₂CH₂-O-CH₂CH₂-O-CH₂CH₂-O-C(=O)-NH-CH₂CH₂-OH |
| 22 | HO-CH₂CH₂-NH-C(=O)-O-CH₂CH₂-O-CH₂CH₂-O-C(=O)-NH-CH₂CH₂-OH |

Synthesis of linear acid-degradable polymers for protein-loaded particle preparation

SEQUENCE LISTING

<160> NUMBER OF SEQ ID NOS: 8

<210> SEQ ID NO 1
<211> LENGTH: 16
<212> TYPE: PRT
<213> ORGANISM: Artificial
<220> FEATURE:
<223> OTHER INFORMATION: SV40 large T antigen nuclear localization
      signal

<400> SEQUENCE: 1

Pro Pro Lys Lys Lys Arg Lys Val Pro Pro Lys Lys Lys Arg Lys Val
1               5                   10                  15

<210> SEQ ID NO 2
<211> LENGTH: 11
<212> TYPE: PRT
<213> ORGANISM: Artificial
<220> FEATURE:
<223> OTHER INFORMATION: HIV TAT protein nuclear localization signal
      peptide

<400> SEQUENCE: 2

Tyr Gly Arg Lys Lys Arg Arg Gln Arg Arg Arg
1               5                   10

<210> SEQ ID NO 3
<211> LENGTH: 19
<212> TYPE: PRT
<213> ORGANISM: Artificial
<220> FEATURE:
<223> OTHER INFORMATION: endoplasmic reticulum-targeting signal peptide

<400> SEQUENCE: 3

Lys Asp Glu Leu Ala Lys Asp Glu Leu Ala Lys Asp Glu Leu Ala Lys
1               5                   10                  15

Asp Glu Leu

<210> SEQ ID NO 4
<211> LENGTH: 28
<212> TYPE: PRT
<213> ORGANISM: Artificial
<220> FEATURE:
<223> OTHER INFORMATION: cytochrome C oxidase mitochondrial-targeting
      signal peptide

<400> SEQUENCE: 4

Ser Val Thr Thr Pro Leu Leu Leu Arg Gly Leu Thr Gly Ser Ala Arg
1               5                   10                  15

Arg Leu Pro Val Pro Arg Ala Lys Ile His Ser Leu
            20                  25

<210> SEQ ID NO 5
<211> LENGTH: 16
<212> TYPE: PRT
<213> ORGANISM: Artificial
<220> FEATURE:
<223> OTHER INFORMATION: PTS1 peroxisome-targeting signal peptide

<400> SEQUENCE: 5

Ser Lys Leu Ala Ser Lys Leu Ala Ser Lys Leu Ala Ser Lys Leu Ala
1               5                   10                  15

<210> SEQ ID NO 6
<211> LENGTH: 19
<212> TYPE: PRT
<213> ORGANISM: Artificial
<220> FEATURE:
<223> OTHER INFORMATION: cell membrane-targeting signal peptide

<400> SEQUENCE: 6

Lys Leu Asn Pro Pro Asp Glu Ser Gly Pro Cys Met Ser Cys Lys Cys
1               5                   10                  15

Val Leu Ser

<210> SEQ ID NO 7
<211> LENGTH: 20
<212> TYPE: PRT
<213> ORGANISM: Artificial
<220> FEATURE:
<223> OTHER INFORMATION: GAP-43 cell membrane-targeting signal peptide

<400> SEQUENCE: 7

Met Leu Cys Cys Met Arg Arg Thr Lys Gln Val Glu Lys Asn Asp Glu
1               5                   10                  15

Asp Gln Lys Ile
            20

<210> SEQ ID NO 8
<211> LENGTH: 8
<212> TYPE: PRT
<213> ORGANISM: Artificial
<220> FEATURE:
<223> OTHER INFORMATION: Ovalbumin derived peptide displayed by antigen
      presenting cells

<400> SEQUENCE: 8

Ser Ile Ile Asn Phe Glu Lys Leu
1               5

MAIN CHAIN ACID-DEGRADABLE POLYMERS FOR THE DELIVERY OF BIOACTIVE MATERIALS

CROSS-REFERENCE TO RELATED APPLICATIONS

This application claims priority to, is a national stage application of, and incorporates by reference PCT Application No. PCT/US2007/068284 filed on May 4, 2007, which claims priority of U.S. Provisional Patent Application No. 60/798,177, filed on May 5, 2006. This application is also a continuation-in-part and incorporates by reference co-pending divisional U.S. patent application Ser. No. 11/388,924, filed on Mar. 28, 2006.

STATEMENT OF GOVERNMENT SUPPORT

This invention was made during work partially supported by National Institutes of Health (Grant RO1GM44885-16) and the U.S. Department of Energy under Contract No. DE-AC02-05CH11231. The government has certain rights in this invention.

REFERENCE TO SEQUENCE LISTING

This application also incorporates by reference the attached sequence listing containing cellular targeting sequences in electronic and paper form, hereby certified as identical copies.

BACKGROUND OF THE INVENTION

1. Field of the Invention

This invention generally relates to the field of main chain acid-degradable polymers for use in delivery of bioactive materials such as antigens, DNA and other therapeutics.

2. Description of the Related Art

Most materials for drug delivery systems are based on polyesters, which break down gradually for a slow consistent release of drug over time. However, it is important in many applications that the therapeutic be delivered and released quickly in the slightly acidic environment of endosomes or tumor tissue. Therefore several drug delivery systems have been designed to release their payload, small drugs or large biotherapeutics, upon a change in pH. Many different strategies have been employed such as attachment of the drug to a scaffold using a pH sensitive linkage, and encapsulation of the therapeutic in liposomes, micelles and particles that break apart or swell in an acidic environment leading to drug release.

Ideal drug delivery systems might have multiple functions, such as targeting the disease site and delivering the therapeutic to a specific site. Currently, there are several potential vehicles for drug delivery that are under investigation, each with their own set of advantages and disadvantages. Most materials for drug delivery systems are based on ester, amide or carbonate linkages, which break down gradually via base catalyzed hydrolysis for a slow consistent release of drug over time. However, there is a potential risk that extended clinical use of conjugates containing non or slow biodegradable polymer fragments can lead to long-term vacuolization. To date, none of the available materials combines all the desirable properties such as, low immunological response, low toxicity and complete biodegradability.

Furthermore, few examples of drug delivery systems are based on polymers that can degrade into small molecules triggered by a small change in pH. Such polymers include poly(acetals) (see Brocchini et al, U.S. Pat. No. 6,828,412), poly(ketals) (see Khaja et al., *Biomacromolecules*, ASAP Article 10.1021/bm061234z S1525-7797(06) 01234-7 and Murthy et al., *Bioconjugate Chem.*, 14 (2), 412-419, 2003), and polyorthoesters (see Ng, S., Y.; Taylor, M., S.; Heller, J. *Macromolecules* 1997, 30, 770-772). It is therefore of interest to develop another class of polymers, which result in full main-chain degradation and that exhibit an even faster degradation and are simple to prepare.

Polycations are a leading class of nonviral gene-delivery vehicles because of their molecular diversity that can be modified to tune their physiochemical properties. Polycations can easily condense DNA through ionic interaction. It was also observed that cationic particles are internalized by cells more easily than neutral ones. One novel class of cationic polymers, which is used for gene delivery, is poly(amidoamines). Poly(amidoamines) possess many desirable properties, such as water solubility, biodegradability, and low cytotoxicity for the development of site-specific gene delivery. Their toxicity was found in number of tests to be constantly lower by two or three orders of magnitude than that of poly-L-lysine. Enhanced degradability of the poly(amidoamines) not only improves biocompatibility but may also help the release of genes from the polymeric scaffold.

Another potential application of these acid-degradable polymer backbones is protein vaccine delivery. The development of protein-based vaccines requires a drug delivery system that undergoes degradation in mildly acidic environment of, for example, tumor and lysosomes. Currently, most available polymers cannot fulfill this requirement because they are composed of linkages that degrade by base catalyzed hydrolysis. Therefore, development of acid degradable polymers, preferably degrading with the formation of nontoxic, readily cleavable or metabolizable products, is of great need. A particle system based on polyacrylamide polymer cross-linked with acid degradable cross linker, has previously been reported for the delivery of proteins. Acid degradable protein loaded polymer particles showed promising results for antigen-based vaccine.

Others have attempted and describe degradable polymers such as Brocchini et al. in U.S. Pat. No. 6,828,412, using high amounts of polyethylene glycol to increase solubility and result in large PEG chain degradation products.

However, one limitation with previous particle systems is the possible long lasting circulation of polyacrylamide after the delivery of protein. To overcome this problem, the present invention describes a completely degradable polymer system, based on polymers such as polyamidoamines, polyureas and polyurethanes.

BRIEF SUMMARY OF THE INVENTION

The present invention is directed to acid-degradable polymers for application in the delivery of proteins, vaccines, drugs (such as the anticancer drugs cisplatin, paclitaxel or taxotere), and other bioactive materials. In a preferred embodiment, the acid-degradable polymers comprise acid-degradable condensation polymers that are designed to deliver bioactive materials upon hydrolysis of an acetal or ketal linkage at pH 5 to pH 7.4. The polymer compositions are made using a bifunctional A-A monomer and another bifunctional B-B monomer resulting in acid-degradable step-growth polymers containing an acid-degradable linkage in each repeating unit. The polymers could be processed to form particles or implants for the pH dependent controlled release of small drug or biotherapeutics. These polymers could also be used as scaffolds for drug conjugation or complexation designed to release their drug at mild pH values.

The polymers of the current invention are designed to degrade into small molecules and release their contents in response to the mild acidic conditions found in lysosomes, tumors, inflammatory tissues and the lysosomes. The present polymers will hydrolyze at a preferred pH range of 4.5 to 6.8, more preferably pH 5.0 to 6.0. Preferably, the polymers will completely hydrolyze within 24 hours at pH 5.0, or conditions such as in the lysosome, and release their encapsulated or bound contents after entering a cell.

The current invention specifically describes the synthesis of acid-degradable polyamides, polyureas, polyurethanes and polyamidoamines, that hydrolyze under acidic conditions.

In one embodiment, the synthesis of different acid degradable bisacrylamide monomers, reacted with piperazine by Michael addition polymerization resulting in a series of pH sensitive polyamidoamines that are used as scaffolds for various drug delivery systems. These polymers have an acetal or ketal linkage in their backbone, which degrades by acid catalyzed hydrolysis into low molecular weight compounds that can be completely excretable. The rate of hydrolysis of these polymers can be changed by varying the ketal linkage from slow degrading to fast degrading and thus providing a wide range of release kinetics for drug delivery.

In another embodiment, the synthesis of an acid degradable diamine monomer that is prepared and reacted with several diisocyanates and bis(p-nitrophenyl carbonates) [as in the Examples for polyureas and polyurethanes] results in a variety of pH sensitive polymers with different solubilities. Herein is also described another class of polymers based on polyureas and polyurethanes that exhibit fast degradation and are simple to prepare and completely degradable. The polymers as well as their degradation products were characterized. The degradation of these polymers into small molecules was monitored at pH 7.4 and pH 5 over time demonstrating that they are stable at physiological pH but break down quickly in mildly acidic environments making these polymers promising candidates for drug delivery systems.

The present invention thus provides an acid degradable polymer composition for delivering a bioactive molecule, comprising: an acid degradable step-growth polymer, having structure (I) $R^1R^2C(OR^3(NR^4)_2$ in each repeating unit, wherein $R^1$ and $R^2$ can be H, $CH_3$, a substituted or unsubstituted alkyl, an aryl, a substituted aryl or an aryl alkyl group, $R^3$ can be $(CH_2)$, where n=2-6, or $(CH_2CH_2(OCH_2CH_2)_n$, where n=1-3, or $(CH_2-CH(CH_3)-CH_2)$, and $R^4$ is H, $CH_3$, or $CH_2CH_3$. In one embodiment, the acid degradable polymer is a polyamide. In other embodiments, the polymer is a polyurethane.

In a preferred embodiment, the acid degradable polymer composition, $R^1$ and $R^2$ are $CH_3$, $R^3$ is $(CH_2)_n$ where n=2-4, or $(CH_2-CH(CH_3)-CH_2)$, and $R^4$ is H, $CH_3$, or $CH_2CH_3$.

The present invention also provides a method of preparing a step-growth acid-degradable composition for delivering a bioactive material to a cell, comprising the steps of (a) preparing a mixture which contains an A-A monomer, a B-B monomer, wherein at least one of the monomers has an acid-degradable linkage; (b) polymerizing the monomers to form a polymer wherein each repeating unit contains the acid-degradable linkage; (c) forming particles of the polymer in the presence of a bioactive material; and (d) recovering the resulting polymer particles having bioactive material bound or entrapped thereto. In a preferred embodiment the AA and BB monomers are used in 1:1 stoichiometry.

BRIEF DESCRIPTION OF THE DRAWINGS

FIG. 12 shows some of the expected degradation products for each polymer upon hydrolysis.

DESCRIPTION OF THE PREFERRED EMBODIMENT

Definitions

Figure 1:
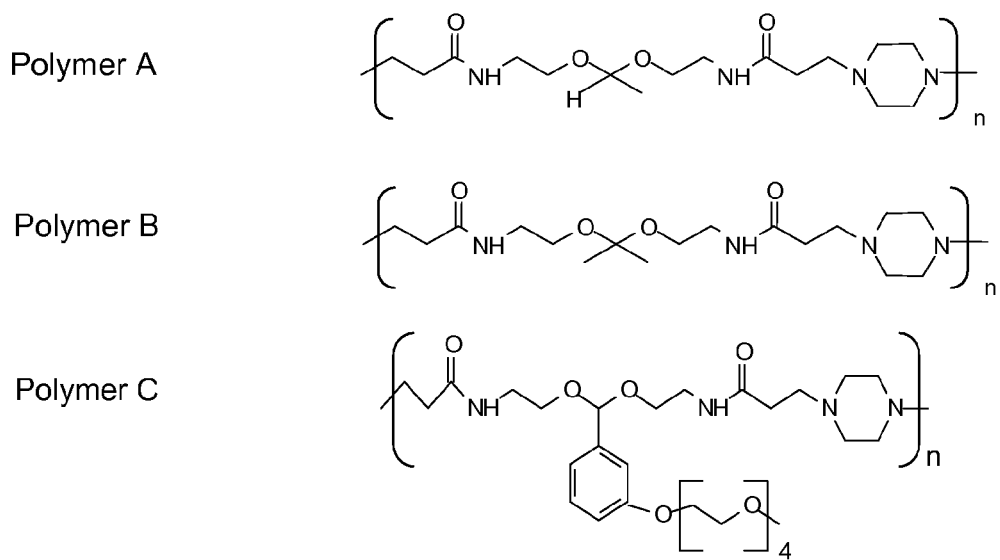
FIG. 1 shows the repeating units for the Polymer A, B and C.

The term "bioactive material" herein refers to a composition having a physiological effect on a cell, particularly a protein antigen, DNA, an enzyme or other organic molecule.

The term "acetal" herein refers to a geminal diether in which both ether oxygens are bound to the same carbon.

The term "acryl" or "acryloyl" herein refers to the general structure $(CH_2=CH-CO-)$.

The term "aryl" herein refers to a homocyclic aromatic, whether or not fused, having 6 to 12 carbon atoms optionally substituted with one to three substituents, wherein said substituents are preferably N or O, or unsubstituted.

The term "alkyl" herein refers to an aliphatic linear or branched chain univalent groups of the general formula $C_nH_{2n+1}$ derived from aliphatic hydrocarbons such as methyl $CH_3$, ethyl $C_2H_5$, propyl $C_3H_7$, 2-methyl propyl $C_4H_{11}$, and the like or cyclic aliphatic univalent groups of the general formula $C_nH_{2n-1}$ derived from cyclic aliphatic hydrocarbons, such as cyclopropyl $C_3H_5$, cyclopentyl $C_5H_9$ and the like, where n is between 2 and 20.

The term "AA monomer" herein refers to a bifunctional monomer containing two reactive functional groups A, for example if A is a primary amino group, the AA monomer is a primary diamine.

The term "BB monomer" herein refers to a bifunctional monomer containing two reactive functional groups B, for example if B is an isocyanate group, the BB monomer is a di-isocyanate.

The terms AA monomer and BB monomer are generally used to depict monomers AA and BB in which the functional groups A and B are mutually reactive to form a covalent chemical bond.

The term "amine-reactive electrophile" herein refers to an electrophile capable of reaction with an amine.

The term "amine-reactive functionality" herein refers to a structure having a functional group capable of forming a covalent bond by reaction with an amine.

The term "loading efficiency" herein refers to the percentage of the starting amount of bioactive material that is encapsulated per milligram of the drug delivery systems. This may be expressed in terms of μg material/mg drug delivery system, on average, based on the starting bioactive material/polymers ratio.

Introduction

In one embodiment, the present invention provides an acid-degradable step-growth polymer comprising an acid degradable, pH sensitive backbone incorporating a group having an acetal or ketal linkage therein, more specifically a group having the structure (I), in each repeating unit of the polymer. This group is designed to remain largely stable in plasma at neutral physiological pH (about 7.4), but degrade intracellularly by hydrolysis in the more acidic environment of the endosome or lysosome (about pH 5.0-6.0.). The polymers exhibit main-chain degradation, whereby the resulting degradation products of the main-chain are largely small molecules.

To facilitate main-chain degradation, each repeating unit in the acid-degradable polymers incorporates structure (I).

The acid-degradable step-growth polymers are prepared using an AA and BB monomer, wherein at least one of the monomers, preferably the AA monomer, contains structure (I). The polymers are prepared generally by step-growth, or condensation reaction. Preferably the acid-degradable step-growth polymers are polyamides, polyureas, polyurethanes, or polyamidoamines. In a preferred embodiment, the polymer is a polyamidoamine.

In a preferred embodiment, the acid-degradable step-growth polymers are processed to deliver a bioactive material. In a preferred embodiment, polymer particles hydrolyze under acidic conditions and release the bioactive material in response to the mildly acidic conditions, found in the body such as in tumors, inflammatory tissues and in cellular compartments such as lysosomes and phagolysosomes of antigen presenting cells.

In a preferred embodiment, the bioactive material includes but is not limited to, antigens, proteins, polynucleotides, polypeptides, peptoids, small drug molecules and other bioactive material.

A. Acid-Degradable Polymers

In a general embodiment, the main chain of the acid-degradable step-growth polymers of the invention contains Structure (I) in each repeating unit. Structure (I) has a structure

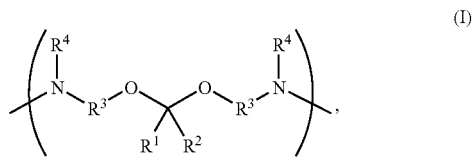

wherein $R^1$ and $R^2$ can be H, $CH_3$, an alkyl or substituted alkyl, an aryl alkyl or a substituted aryl group, wherein $R^1$ and $R^2$ can be the same or different, $R^3$ can be $(CH_2)_n$, where n=2-6, or $(CH_2CH_2(OCH_2CH_2)_n$, where n=1-3, or $CH_2$—$CH(CH_3)$—$CH_2$, and $R^4$ is H, $CH_3$, or $CH_2CH_3$. In a preferred embodiment, $R^1$ and $R^2$ are $CH_3$, $R^3$ is $CH_2$—$CH(CH_3)$—$CH_2$ or $(CH_2)_n$ where n=2-4, and $R^4$ is $CH_3$, or $CH_2CH_3$.

The acid-degradable polymer is made by the condensation polymerization of an AA bifunctional monomer and a BB bifunctional monomer, wherein the AA monomer acts as a bis-nucleophile and the BB monomer acts as a bis-electrophile. At least one of the monomers contains structure (I).

In one embodiment, the AA monomer is a bisnucleophile and is reacted with a BB monomer, a bis electrophile having two amine-reactive functionalities containing Structure (I).

In a preferred embodiment, the AA monomer is any primary/secondary diamine monomer, and reacted with a BB monomer containing Structure (I). In a preferred embodiment in such a case, both $R^1$ and $R^2$ are $CH_3$. In another preferred embodiment, $R^1$ is H, and $R^2$ is an aryl alkyl group, such as Compound 8, the triglyme compound in Example 2. In another embodiment, $R^1$ is H, and $R^2$ is a methyl or alkyl group, such as Compound 12.

In one embodiment, the AA monomer is a bisnucleophile and the BB monomer is the amine-reactive bis-electrophile containing Structure (I). The AA monomer bis-nucleophile can be or is derived from any of the following:

Any primary/secondary amine   Any diol   Any dithiol

(II)

(III)

(IV)

(V)

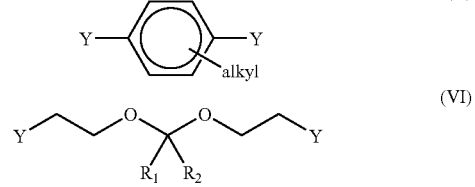

(VI)

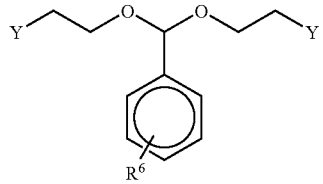
(VII)

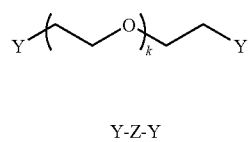
(VIII)

Y-Z-Y (IX)

wherein Y=OH, SH, NH$_2$ or NH-alkyl, wherein in (VII) R$^6$=—O(CH$_2$CH$_2$O)$_m$—R$^5$ and m=1-5, R$^5$ is C$_2$-C$_6$ alkyl or CH$_3$; wherein in (VIII) k=1-6; and wherein in (IX) Z is a functional group unaffected by polymerization conditions that can be further modified post polymerization.

In a preferred embodiment, the AA monomer is a primary/secondary diamine and the BB monomer has the general formula of X—R—X, wherein X is the amine-reactive functional group. Examples of BB monomers include but are not limited to, diisocyanate (OCN—R—NCO), phosgene (Cl—CO—Cl), S=C=N—R—N=C=S, and monomers having the following structures:

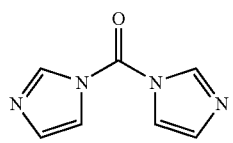
(X)

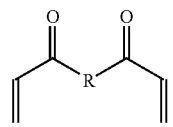
(XI)

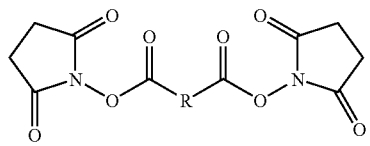
(XII)

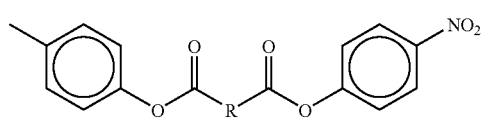
(XIII)

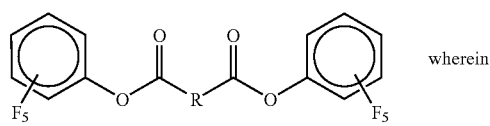
(XIV)

wherein

R = {

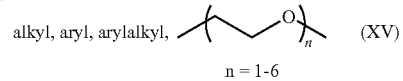 alkyl, aryl, arylalkyl, (XV)

n = 1-6

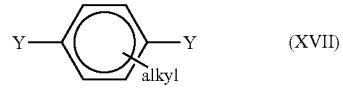 (XVII)

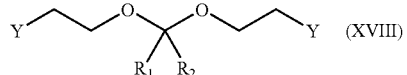 (XVIII)

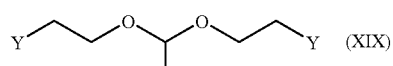 (XIX)

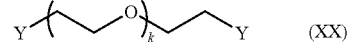 (XX)

Y—Z—Y (XXI)

Y-alkyl-Y (XXII)

Y-aryl-Y (XXIV)

} wherein Y= nothing or Y=O, NH, S, N-alkyl, in (XVIII) R$^1$ and R$^2$ can be H, CH$_3$, an alkyl or substituted alkyl, an aryl alkyl or a substituted aryl group, wherein R$^1$ and R$^2$ can be the same or different, in (XX) k=1-6; in (XIX) R$^6$ is —O(CH$_2$CH$_2$O)$_m$—R$^5$ and m=1-5 and R$^5$ is CH$_3$ or C$_2$-C$_6$ alkyl; and in (XXI) Z=a functional group unaffected by polymerization conditions that can be further modified post polymerization. In a preferred embodiment, Z may be an alkyl or aryl group also containing a pendant protected hydroxyl, amine or carboxyl group.

In another embodiment, the AA monomer contains Structure (I), and is reacted with a BB monomer also containing Structure (I). In a preferred embodiment, the AA monomer is a primary/secondary diamine and the BB monomer contains amine-reactive functional groups. It is contemplated that known compounds containing Structure (I) may be useful in making the present polymers. For example, the triglyme intermediate monomer, Compound 8, used in polymer C was previously described and used as an acid-degradable crosslinker in microgel particles in co-pending U.S. patent application Ser. No. 10/401,496, filed on Mar. 28, 2003, currently allowed. In an in vivo study, particles made using the triglyme crosslinker were shown to provide immunity against tumors in mice, and an enhanced survival rate over the use of protein alone was observed. Standley S. et al., Acid-degradable particles for protein-based vaccines: enhanced survival rate for tumor-challenged mice using ovalbumin model, *Bioconjug Chem.* 2004 November-December; 15(6):1281-8. In the present invention, polymer C is used to create main chain degradable polymers which will result in smaller degradable products.

Compound 3, used as a monomer in Example 2, was also described in Kwon, Y J et al., Directed antigen presentation using polymeric microparticulate carriers degradable at lysosomal pH for controlled immune responses, *Mol. Pharm.* 2005 January-February; 2(1):83-91, and used as an acid-degradable crosslinker in microgel particles. The compound is used herein not as a crosslinker but as a monomer for main chain acid degradable polymers.

In a preferred embodiment, the polymer is Compound A, B, C, 29, 30 or 31.

The polymers are prepared generally by step-growth, or condensation polymerization reaction. Typically step-growth polymerization is a polymerization process that involves a chemical reaction between multifunctional monomer molecules. One variety of step-growth polymerization is called condensation polymerization and the product a condensation polymer because the chemical reaction by which the monomer molecules bond is often but not always a condensation reaction that produces a small molecule byproduct. A multifunctional monomer is a molecule that has more than one potential reactive site through which it can form intermolecular chemical bonds. AA and BB monomers each have two functional groups (e.g., two amino groups, two isocyanates, or two active esters) whereby each monomer can possibly form two bonds to link into a chain structure. Preferably the acid-degradable step-growth polymers are polyamides, polyureas, polyurethanes, or polyamidoamines. In a preferred embodiment, the polymer is a polyamidoamine. In another preferred embodiment, the acid degradable polymer is a polyamide. In yet another preferred embodiment, the polymer is a polyurea or polyurethane.

In general, the design of the AA and BB monomers also reflects such factors as ease of synthesis, solubility, commercially available reagents, the type acid-degradable polymer desired, the loading efficiency, dispersion of drug delivery systems comprised of the polymers, toxicity and the hydrolysis rates of the acetal linkage.

In a preferred embodiment, the degradation products are small molecules with a molecular mass of up to 10,000 daltons or lower, more preferably 1000 daltons, and most preferably 400 daltons or lower. Since the present polymers are designed to degrade within the main chain, in a preferred embodiment, the degradation product(s) should be non-immunogenic and non-toxic, for example, with the size and/or toxicity levels of those described in the Examples.

1. Acid Degradable Linkages

The present acid degradable monomers and polymers described herein should have a significantly lower rate of degradation in solution at pH 7.0 than at pH 5.

These polymers have an acetal or ketal linkage in their backbone, which degrades by acid catalyzed hydrolysis into lower molecular weight compounds that can be completely excretable. The rate of hydrolysis of these polymers can be changed by varying the acetal or ketal linkage from slow degrading to fast degrading, thus providing a wide range of release kinetics for drug delivery.

Thus, it is contemplated that a variety of acid degradable linkages with different acid-sensitivities can be incorporated into the polymer backbones using this technology, allowing for excellent control of the rate of polymer hydrolysis.

2. Hydrolysis of the Polymers

Drug delivery systems comprised of the polymers can be hydrolyzed to release their contents in a pH dependent manner. A feature of the present degradable polymers is also the main chain of the present polymer hydrolyzes into small molecules in a pH dependant manner. In a preferred embodiment the polymers should preferably have a degradation half-life at pH 5.0 of 5 minutes to 24 hours at 37° C., but a longer half life at pH 7.4 of at least 12 hours to 250 days. In the Examples, the degradable polymers have degradation rates at pH 5.0 ranging from half-life of 5 minutes to 100 minutes to 4.4 days to over 80 days.

In some embodiments, it may be useful for the polymers to have a half-life at pH 5.0, 37° C. of about 24 hours, and a half-life at pH 7.4, 37° C. of about 250 days, in order to facilitate the slow release of bioactive materials. In other embodiments, it is contemplated that the half-life of polymer degradation at pH 5.0, 37° C. preferably be 5-30 minutes, and even more preferably be less than 5 minutes and a half-life at pH 7.4, 37° C. of about 24 hours in order to quickly release the bioactive materials.

The acceleration of the hydrolysis kinetics of acetals from pH 7.4 to pH 5.0 is expected because the hydrolysis of the acetal is proportional to the hydronium ion concentration, which should increase between pH 7.4 and pH 5.0. The kinetics of acetal hydrolysis can be easily manipulated by introducing the appropriate electron withdrawing or donating groups and therefore it is possible to engineer degradable polymers that have hydrolysis rates tailor-made for a given application.

A kinetic factor that may be taken into account when designing acid degradable polymer backbones is the acid degradable linkage's speed of hydrolysis in solution. In an embodiment where the goal is to hydrolyze the polymer and rapidly release the bioactive material, the acetal should preferably hydrolyze within 5-30 minutes at pH 5.0 at 37° C. This timescale is chosen because it is approximately the amount of time taken for a phagocytosed drug delivery system to be trafficked to cellular compartments such as lysosomes. In a preferred embodiment, these particles will degrade rapidly in the lysosome and cause lysosomal destabilization. Having a particle that degrades too slowly will increase its residence time in the lysosome and provide the lysosomal enzymes an increased chance of hydrolyzing the bioactive material before reaching the cytoplasm through lysosomal disruption. Therefore, in a preferred embodiment, the polymer should hydrolyze fairly rapidly at a preferred range of pH 7.4 to 4.5 and even more preferably between pH 6.8 to 4.5.

The present degradable polymers are largely stable at pH higher than 7.4 but hydrolyze at a pH preferably about 5. The present degradable polymers do not require aqueous solubility of greater than 50 mg/ml as in previous applications.

3. Bioactive Materials

In a preferred embodiment, the invention contemplates entrapping or conjugation of such bioactive materials including but not limited to, nucleotides, oligonucleotides, polynucleotides, ribonucleotides, amino acids, oligopeptides, polypeptides, peptoids, proteins, antigens, plasmid DNA, growth factors and hormones, interleukins, immunostimulatory agents, drugs, vaccines, neuromodulatory agents such as neurotransmitters, stimulatory and adrenergic agents, enzymes, proteases, anticancer and antitumor agents, imaging agents, diagnostic agents, antiviral agents and antibacterial agents as well as combinations of two or more of these species.

In specific preferred embodiments, the bioactive material is selected from the group consisting of: nucleotides, oligonucleotides, polynucleotides, proteins, oligopeptides, polypeptides, immunostimulatory agents, vaccines, antigens, anti-viral agents, protein antigens, anticancer agents and anti-tumor agents.

One or more of these bioactive materials can be conjugated to the polymer chains. The linkage between the polymer chain and the bioactive molecule can be designed to be cleaved under various physiological conditions. The bioactive material can also be adsorbed onto the surface of drug delivery systems, or reacted to the surface of the drug delivery systems. The bioactive material can also be physically trapped inside the drug delivery systems comprised of the degradable polymers.

4. Drug Delivery Systems

In a preferred embodiment, the degradable polymers are made into particles for such applications as vaccine delivery. Typical formulations for therapeutic agents incorporated in these delivery systems are well known to those skilled in the art and include but are not limited to solid particle dispersions, encapsulated agent dispersions, and emulsions, suspensions, liposomes or microparticles, wherein said liposome or microparticle comprise a homogeneous or heterogeneous mixture of the therapeutic agent. The amount of the drug that is present in the device, and that is required to achieve a therapeutic effect, depends on many factors, such as the minimum necessary dosage of the particular drug, the condition to be treated, the chosen location of the inserted device, the actual compound administered, the age, weight, and response of the individual patient, the severity of the patient's symptoms, and the like.

In a preferred embodiment, the degradable polymers made into particles that are 40 to 100 nm In general, particles can be synthesized by various techniques, such as inverse emulsion, double emulsion or spray drying methods according to the procedures described by Liu, R.; Ma, G.; Meng, F.; Su, Z. *J. Controlled Release* 2005, 103, 31-43 and Witschi, C.; Mrsny, J. R. *Pharm. Res.* 1999, 16, 382-390. In a preferred embodiment, the particles are made by either double emulsion or inverse emulsion polymerization process.

Inverse emulsion and the double emulsion method can be used to produce particles from sub-micrometer to multi-micrometer sizes; a preferable size range is from 30 nm to 5000 nm, more preferably 30 nm to 2000 nm, and most preferably 40 to 200 nm.

Particles can be synthesized by inverse microemulsion polymerization according to the procedure described by Kriwet, B.; Walter, E.; Kissel, T.; *J. Control Release,* 1998, (56), 149-158, which describes synthesis of bioadhesive poly(acrylic acid) nano- and microparticles using an inverse emulsion polymerization method for the entrapment of hydrophilic drug candidates. The solubility of both monomers, polymerizable groups are very important as all of the polymerizable components in an inverse emulsion polymerization must be sufficiently water soluble.

In a preferred embodiment, microemulsion polymerizations with hexane as the continuos phase and surfactants such as SPAN™ 80 (sorbitan monooleate), TWEEN™ 80 (polyethyleneglycol-sorbitan monooleate), dioctyl sulfosuccinate (AOT) and Brij 30 (Polyoxyethylene (4) Lauryl ether) (all from Sigma Aldrich, St. Louis, Mo.) can be used to produce particles.

During inverse microemulsion polymerization, a small amount of water is dispersed into an organic phase and stabilized by surfactants. Sonication before polymerization for about 5 minutes will insure the correct particle size, which will cover a range of sizes, within the range of about 100 nm-5 μm, preferably 30 nm-2000 nm. The AA and BB monomers are then polymerized in the aqueous phase in the presence of the bioactive material and an initiator molecule or radical source. Since polymerization is initiated and contained within water droplets, mainly spherical crosslinked microgel particles containing entrapped bioactive material are produced. To adjust particle size, either longer sonication time or larger surfactant concentration will decrease the microgel particle size.

During the double emulsion method, first, the polymer is dissolved in organic solvent along with the surfactants. Then, a small amount of aqueous solution containing the bioactive materials is dispersed into the organic/polymer phase by sonication forming a primary water-in-oil emulsion. This primary emulsion is then dispersed into a larger amount of water containing stabilizers to form a secondary water-in-oil-in-water emulsion. After forming the secondary emulsion, the solution is stirred until the organic phase evaporates. When evaporated, the polymer collapses around the aqueous bioactive material solution forming therapeutic-loaded particles.

The particles can also be obtained by an inverse emulsion polymerization using a method modified from the method described in Clark, H. A.; Hoyer, M.; Philbert, M. A.; Kopelman, R. *Anal. Chem.* 1999, 71, 4831-4836, hereby incorporated by reference, to produce particles having a homogeneous size range. A continuous phase solution is prepared comprising two surfactants dissolved in an organic solvent. The aqueous phase is prepared as follows. Bioactive material is dissolved in PBS adjusted to pH 9.0 using NaOH. The monomers are then dissolved in the solution. The aqueous phase is then added to the continuous phase dropwise via syringe with constant stirring. After stirring the emulsion, the initiator is added to the mixture and polymerization is allowed to proceed. After polymerization, the organic solvent is removed by rotary evaporation, and the residue is suspended in ethanol to form a milky suspension. The suspension is then centrifuged to pellet the particles. The pellet is washed with ethanol by resuspending and centrifuging again before the pellet is resuspended in ethanol and sonicated in a water bath. After the ethanol is removed, the particles are dried overnight, under vacuum.

In a preferred embodiment, the acid-degradable polymers are processed to form particles comprised of the main chain acid degradable polymers having a bioactive material bound to or entrapped within the formed particles.

In another embodiment, the degradable polymers are made into drug delivery systems such as a small molecule implant, or time-release device or implant. Methods and compositions useful in making or administering an implant or time-release device in vivo are known and used by one having skill in the art. Examples of such methods and compositions are described in U.S. Pat. Nos. 3,976,071; 5,876,452; 7,077,859; 5,021,241, hereby incorporated by reference. For example, the main chain degradable polymers of the invention can be prepared in solid form of a needle or bar-like shape and administered to the body or implanted into the body by injection or an injection-like method and whereby the bioactive material is released at an effective level for a long period of time after administration.

5. Loading and Loading Efficiency of Entrapped Bioactive Materials

Loading efficiency is the amount of bioactive material that is entrapped in or conjugated to within the drug delivery systems comprised of the polymers as compared to the total starting amount of bioactive material placed in the loading reaction.

The loading capacity is the amount of bioactive material contained in the polymer particle, it is generally expressed in mass of bioactive material per unit mass of particle. The loading efficiency and the amount of bioactive material entrapped are important aspects in light of such factors as the amount of bioactive material needed to be delivered to the target for an effective dose and the amount of available bioactive material. A major drawback in previous therapeutics and vaccines is there is often difficulty in obtaining large enough amounts of the therapeutic composition of bioactive material for production. Therefore, it is a goal of the invention to make drug delivery systems with high loading capacities and efficiencies.

In one embodiment, wherein the bioactive material is a small drug molecule for polymer-drug conjugates for applications such as chemotherapy, the degradable polymer particles should exhibit preferred loading as is known in the art. For example, the polymer particles should exhibit high loading efficiency to allow sufficient drug molecules to be conjugated to the polymer or otherwise retained by the polymer without loss of solubility of the overall formulation.

In a preferred embodiment, wherein the bioactive material loaded is DNA material, the loadings and efficiencies of the drug delivery systems should be comparable to other microparticle systems which have efficiencies purported to be about 1-2 µg DNA/mg polymer for 500 nm PLGA particles. (See Garcia del Barrio, G.; Novo, F. J.; Irache, J. M. *Journal of Controlled Release* (2003), 86(1), 123-130). It is estimated that at least about 3,000-7,000 molecules of DNA can be encapsulated within a single degradable polymer particle of the present invention, if the DNA encapsulated was 6,000 bp, which has a MW of about 4 million daltons. The loading efficiencies for the amount of DNA material entrapped in degradable particles of the preferred embodiment should preferably be at least 40%, more preferably at least 50% and even more preferably at least 54%. Loadings for bacterial DNA for immunostimulation purposes should be around 1-30 µg DNA/mg.

In a preferred embodiment, wherein the bioactive material loaded is protein, the loading efficiencies for the amount of protein entrapped in particles comprised of the acid degradable polymers of the preferred embodiment should be at least 20%, preferably at least 40%, more preferably around 50%.

6. Toxicity of Polymers and Polymer Degradation Products

Use of this invention in human and mammalian therapeutics brings up issues of the toxicity of these polymers. The viability of cells can be measured by the ability of mitochondria in metabolically active cells to reduce yellow tetrazolium salt (MTT) in the classical MTT assay to form formazan crystals.

In a preferred embodiment, the target cells should preferably exhibit at least 50% viability after 24 hours of incubation with the polymers of the invention, more preferably at least 70% viability after 24 hours, even more preferably at least 80% viability and most preferably more than 90% viability after 24 hours according to the MTT assay.

Figure 21:
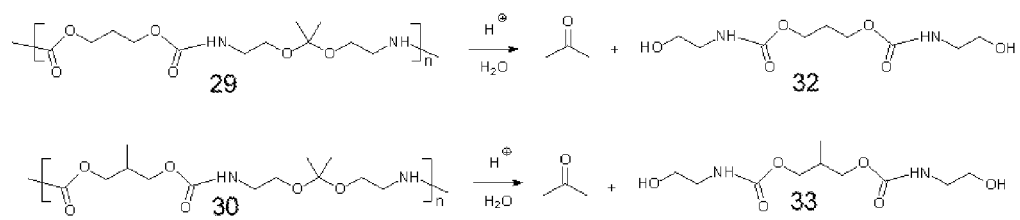
FIG. 21 shows some of the expected degradation products from the polymers of FIG. 20.

Polymers with high MW are not easily excreted from the body, therefore another aspect of the invention is to make polymers that are easily and safely excreted by the body after being degraded in the acidic environments. In general it is preferred that the polymers degrade into many small molecules that are non toxic and readily excreted from the body. The degradation products of the present degradable polymers of the invention should be easily excreted from body due to the small molecule size of the degradation products produced after hydrolysis of the main chain of the degradable polymers. Therefore another aspect of the invention is to make particles that are easily and safely excreted by the body after being degraded in the acidic cellular compartment. In general it is preferred that the particles degrade into smaller molecules that are 10,000 daltons or less, and that the degradation products are not toxic to a mammalian subject. For example, in a preferred embodiment, the polymers having expected degradation products of acetone and the products shown in FIGS. 12 and 21.

B. Applications for Acid Degradable Polymers Backbones

This strategy for the synthesis of acid degradable polymer backbones has many applications including the delivery of bioactive materials, including but not limited to polynucleotides, polypeptides, proteins, peptides, antibodies, vaccines, antigens, genetic, small drugs or therapeutic agents, into the cytoplasm of phagocytic cells, site of inflammation, tumor tissues, endosomes, or other sites of low pH.

1. Vaccine Therapeutics

In one embodiment, the polymers of the present invention would have applications in vaccine therapeutics and disease prevention. Protein loaded particles prepared using these polymers could be injected into a patient, stimulating phagocytosis by macrophages and antigen presenting cells.

In one embodiment, the acid-degradable polymer particles are delivered to antigen presenting cells and then phagocytosed and trafficked to the lysosome or phagolysosome of the cells. The mild acidic conditions found in lysosomes and phagolysosomes of APCs should cause the acetal group along the polymer backbones to be hydrolysed thereby degrading the particles. This acid hydrolysis of the acid-degradable linkage causes main-chain degradation of the polymers. This swelling of the particles should act to increase the osmotic pressure inside the cellular compartment which causes the cellular compartment to destabilize, thus releasing the bioactive material into the cytoplasm where it is exposed to the MHCl protein. The MHCl protein should then display the bioactive material on the cell surface of the antigen presenting cell and activate cytotoxic T lymphocytes (CTL) which can then recognize virus infected cells that display the bioactive material, thus targeting $TCD^+8$ immune response.

The particles comprised of the acid degradable polymers of the invention would be particularly useful in combating infections that need a strong cytotoxic T lymphocyte response, including diseases such as HIV/AIDS and Hepatitis C infections. Examples of such antigens which can be used as bioactive material and entrapped in the particles of the present invention, include but are definitely not limited to, the TAT protein from HIV, the ENV protein from HIV, the Hepatitis C Core Protein from the Hepatitis C virus, the prostatic acid phosphatase for prostate cancer and the protein MART-1 for melanoma.

Figure 18:
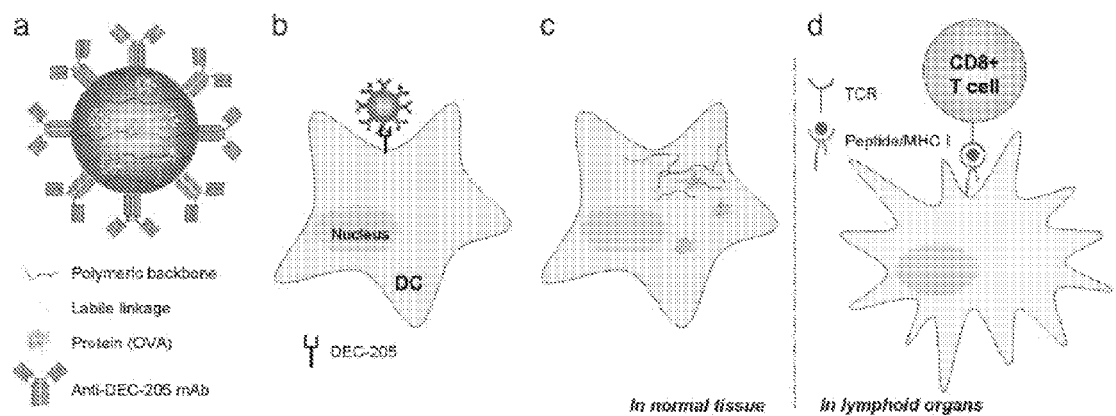
FIG. 18 is a cartoon showing a schematic diagram of enhanced CTL activation by dendritic cell-targeting acid-degradable particles

Referring now to FIG. 18, in one embodiment, the acid-degradable polymers particles enhance CTL activation by dendritic cell (DC)-targeting. In FIG. 18*a* OVA was encapsulated in acid-degradable polymeric particles further conjugated with anti-DEC-205 mAbs monoclonal antibody. In FIG. 18*b*, the particles are taken up by DEC-205 expressing dendritic cells in vivo. In FIG. 18*c*, after hydrolysis in the acidic lysosome of DCs, encapsulated OVA is released into the cytoplasm. FIG. 18*d* shows intracellularly processed OVA-derived peptides are presented as a complex with MHC I and recognized by CD8_T cells with the corresponding T cell receptors in secondary lymphoid organs (e.g., LNs and spleen). After successful ligation, CD8_cells differentiate into CTLs.

In a preferred embodiment, bioactive drug molecules may be temporarily attenuated by incorporation into acid-degradable polymers for applications such as chemotherapy. Drug molecules may be incorporated into the polymers covalently, where the drug molecules are attached to the main polymer chain via labile linkages. Water soluble polymer-drug conjugates will preferably be administered intravenously or orally, and biologically active drug molecules will be released from the polymer upon cleavage of the labile polymer-drug linkages. Drug molecules may also be incorporated noncovalently by entrapment of drugs into particles or implant devices fashioned from water insoluble variants of the acid-degradable polymers. Water insoluble polymers will preferably be administered orally or will be implanted in the body, and drug molecules will be released from the polymer upon degradation of the polymer matrix in which the drug is entrapped or conjugated.

In another embodiment, a signal peptide is attached to the particle. Any suitable signal peptide can be used in the particles of the invention. The peptide should be able to target (i.e., mediate entry and accumulation) a particle to a subcellular compartment and/or organelle of interest. Signal peptides are typically about 5 to about 200, about 10 to about 150, about 15 to about 100, or about 20 to about 50 amino acids in length. Suitable signal peptides include, e.g. nuclear localization signal peptides, peroxisome-targeting signal peptides, cell membrane-targeting signal peptides, mitochondrial-targeting signal peptides, and endoplasmic reticulum-targeting signal peptides, and trans-Golgi body-targeting signal peptides. Signal peptides may also target the particles to any cell surface receptor including e.g. epidermal growth factor receptors (EGFR), fibroblast growth factor receptors (FGFR), vascular endothelial cell growth factor receptor (VEGFR), integrins, chemokine receptors, platelet-derived growth factor receptor (PDGFR), tumor growth factor receptora, and tumor necrosis factor receptors (TNF).

Nuclear localization signal peptides typically comprise positively charged amino acids. Endoplasmic reticulum targeting signal peptides typically comprise about 5 to about 10 hydrophobic amino acids. Mitochondria targeting signal peptides are typically about 5 to about 10 amino acids in length and comprise a combination of hydrophobic amino acids and positively charged amino acids. Peroxisome targeting signal peptides include PTS1, a 3 amino acid peptide and PTS2, a 26-36 amino acid peptide. Examples of signal peptide sequences include but are not limited to the following sequences in Table 1.

TABLE 1

| Target | Source | Sequence |
|---|---|---|
| Nucleus | SV-40 large T antigen | PPKKKRKVPPKKKRKV (SEQ ID NO: 1) |
| Nucleus | Tat protein of HIV | YGRKKRRQRRR (SEQ ID NO: 2) |
| Endoplasmic Reticulum | | KDELA KDELA KDELA KDEL (SEQ ID NO: 3) |
| Mitochondria | Cytochrome C oxidase | SVTTPLLLRGLTGSARRLPVPRA KIHSL (SEQ ID NO: 4) |
| Peroxisome | | SKLA SKLA SKLA SKLA (SEQ ID NO: 5) |
| Cell Membrane | | KLNPPDESGPCMSCKCVLS (SEQ ID NO: 6) |
| Cell Membrane | GAP-43 | MLCCMRRTKQVEKNDEDQKI (SEQ ID NO: 7) |

Signal peptides can be chemically synthesized or recombinantly produced. In general, the nucleic acid sequences encoding signal peptides and related nucleic acid sequence homologues are cloned from cDNA and genomic DNA libraries or isolated using amplification techniques with oligonucleotide primers. Standard techniques are used for nucleic acid and peptide synthesis, cloning, DNA and RNA isolation, amplification and purification. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

In another embodiment, the particles are decorated with a targeting functional group or other cell penetrating peptides to penetrate non-phagocytic cells. For example, targeting functional groups include antibodies, various oligopeptides, or carbohydrate moieties, Cell-penetrating peptides can also include oligopeptides such as oligomers or arginine or polymers rich in arginine motifs.

In one embodiment, immunostimulatory groups are attached and displayed on the particle. Examples of immunostimulatory groups include but are not limited to mannose, plasmid DNA, oligonucleotides, ligands for the Toll receptors, interleukins and chemokines. T-cells activate B-cells to secrete Interleukin-6 (IL-6) to stimulate B cells into antibody-secreting cells.

In another embodiment, targeting antibodies are attached to the particle. Any antibody specific for a target in vivo can be attached to the particle to target and allow particle delivery of the bioactive material.

For example, referring again to FIG. 18, in one embodiment, the acid-degradable polymers particles enhance CTL activation by dendritic cell (DC)-targeting as described above.

2. Gene Therapy

In another embodiment, the polymers of the invention would be used to prepare drug delivery systems for gene therapeutics. The cationic polymers would be especially relevant for this application because polycations can complex with DNA. Since gene therapy involves the delivery of a sequence of DNA to the nucleus of a cell, the particles comprised of these polymers of the invention would be especially suited for this application. Once a polynucleotide is delivered by the drug delivery systems to the cytoplasm, the polynucleotide can undergo translation into a protein. This has the potential, then, to make proteins that are not normally produced by a cell.

In a preferred embodiment, the bioactive material is a plasmid that encodes for a protein or antigenic peptide initially. For example, one would use a plasmid that encodes for a protein that would display antigens for cancer. These proteins are not easy to generate in multi-milligram to gram quantities to be delivered to a patient, therefore using the present particle delivery systems prepared with polymers of the present invention to deliver plasmid DNA encoding these antigens is a preferred alternative.

In addition to encoding for a gene, plasmid DNA has the added characteristic of generating an immune response because plasmid DNA is generated from bacteria. Other potential bioactive materials are CpG oligonucleotides that are also derived from bacterial DNA. Bacterial DNA has two major differences compared with vertebrate DNA: 1) bacterial DNA has a higher frequency of CG dinucleotides in the sequence ($\frac{1}{16}$ dinucleotides in microbial DNA are CG pairs, but only 25% of that is observed in vertebrate DNA); and 2) bacterial DNA is unmethylated as compared to vertabrate DNA which is often methylated. Vertebrate systems will recognize the DNA then as being foreign, and the cell should react as for a bacterial infection. This immune response is manifested in the production of cytokines and interleukins that then go on to activate T cells, B cells, and other cells, proteins, and cellular machinery involved in the immune response.

3. Directing Patient Immune Response Using the Helper T-Cell Response

In a further embodiment, the plasmid DNA used as the bioactive material would have an added interleukin sequence. (Egan, Michael A.; Israel, Zimra R. *Clinical and Applied Immunology Reviews* (2002), 2(4-5), 255-287.) Interleukins are secreted peptides or proteins that mediate local interactions between white blood cells during immune response (B. Alberts et al, *Molecular Biology of the Cell*, 4th ed., Garland Science, 2002). Different interleukins (e.g. IL-12, IL-2) will direct the type of immune response that is generated. IL-6, IL-1, IL-8, IL-12, and TNF-α are secreted by infected macrophages as an immune response and IL-6 serves to activate lymphocytes and increase antibody production. The differentiation of helper T cells into either $T_H1$ or $T_H2$ efffector cells determines the nature of the response. A $T_H 1$ response is characterized by a CTL response; a $T_H2$ response is characterized by antibody production.

It has been shown by Apostolopoulos, V.; McKenzie, I. F. C. *Current Molecular Medicine* (2001), 1(4), 469-474, that activation of the mannose receptors on the surface of APCs leads to enhanced CTL activation. Thus, the addition of the interleukin-2 or 12 (IL-2 or IL-12) gene sequence, and its subsequent translation into an interleukin protein may allow the direction of the type of patient immune response and amplification of the desired CTL response by adding or displaying immunostimulatory groups on the surface of the microgels. Such immunostimulatory groups include but are not limited mannose, plasmid DNA, oligonucleotides, ligands for the Toll receptors, interleukins and chemokines. T-cells activate B-cells to secrete Interleukin-6 (IL-6) to stimulate B cells into antibody-secreting cells.

4. Drug Delivery Systems and Dispersion

Drug delivery systems comprised of the invention may be suspended or stored in a conventional nontoxic vehicle, which may be solid or liquid, water, saline, or other means which is suitable for maintaining pH, encapsulation of the bioactive material for an extended period of time, sufficient dispersion or dilution of the delivery systems and the overall viability of the delivery systems for their intended use.

Preferably the delivery systems comprised of the polymers of the invention are stored in dry state (vacuum dried) and stored at 4° C. for several months. The systems may be dispersed in buffer and sonicated or vortexed for a few minutes to resuspend into solution when needed.

5. Pharmaceutically Effective Delivery and Dosages

The loaded drug delivery systems of the invention can be administered by various suitable means to a patient, including but not limited to parenterally, by intramuscular, intravenous, intraperitoneal, or subcutaneous injection, or by inhalation. The delivery of the systems to a patient is preferably administered by injection once but does not preclude the necessity for multiple injections that would be required to illicit the desired level of immune response. In another embodiment, the delivery system is an implant system, wherein the polymer is implanted into an affected tissue, such as a tumor, and allowed to degrade and release the bioactive material. For example, water insoluble degradable polymers are implanted in the body, and drug molecules will be released from the polymer upon degradation of the polymer matrix in which the drug is entrapped.

The amount of delivery vehicle needed to deliver a pharmaceutically effective dosage of the bioactive material will vary based on such factors including but not limited to, the polymer solubility, the therapeutic loading capacity and efficiency, the toxicity levels of the polymers, the amount and type of bioactive material needed to effect the desired response, the subject's species, age, weight, and condition, the disease and its severity, the mode of administration, and the like.

One skilled in the art would be able to determine the pharmaceutically effective dosage. In general, the amount of bioactive material that could be administered by the delivery systems of the invention is from 1 ng to more than 1 g quantities.

EXAMPLE 1

Synthesis and Characterization of Main-Chain Acid-Degradable Bisacrylamide Polymers A, B and C This example highlights the synthesis of different acid degradable bisacrylamide monomers, which reacted with piperazine by Michael addition polymerization resulting in a series of pH sensitive polyamidoamines that will eventually become scaffolds for various drug delivery systems. These polymers have ketal linkage in its backbone, which degrades by acid catalyzed hydrolysis into low molecular weight compounds that can be completely excretable. The rate of hydrolysis of these polymers can be changed by varying the ketal linkage from slow degrading to fast degrading and thus providing a wide range of release kinetics for drug delivery.

Figure 2:
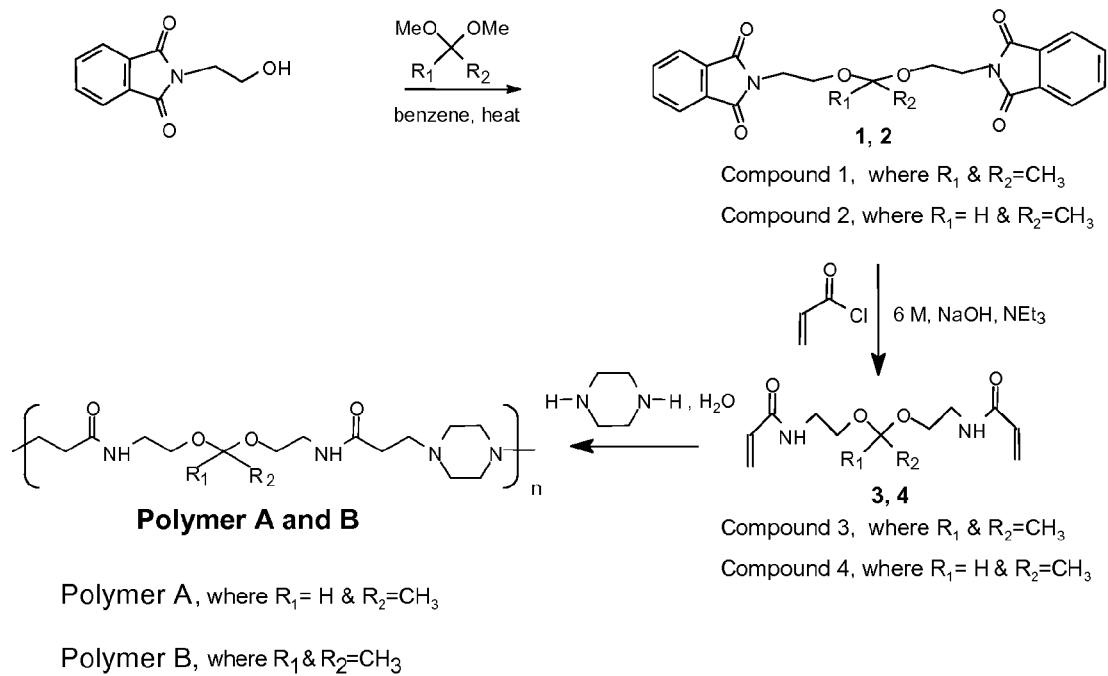
FIG. 2 shows an overall synthetic scheme for the preparation of Polymers A and B.
Figure 3:
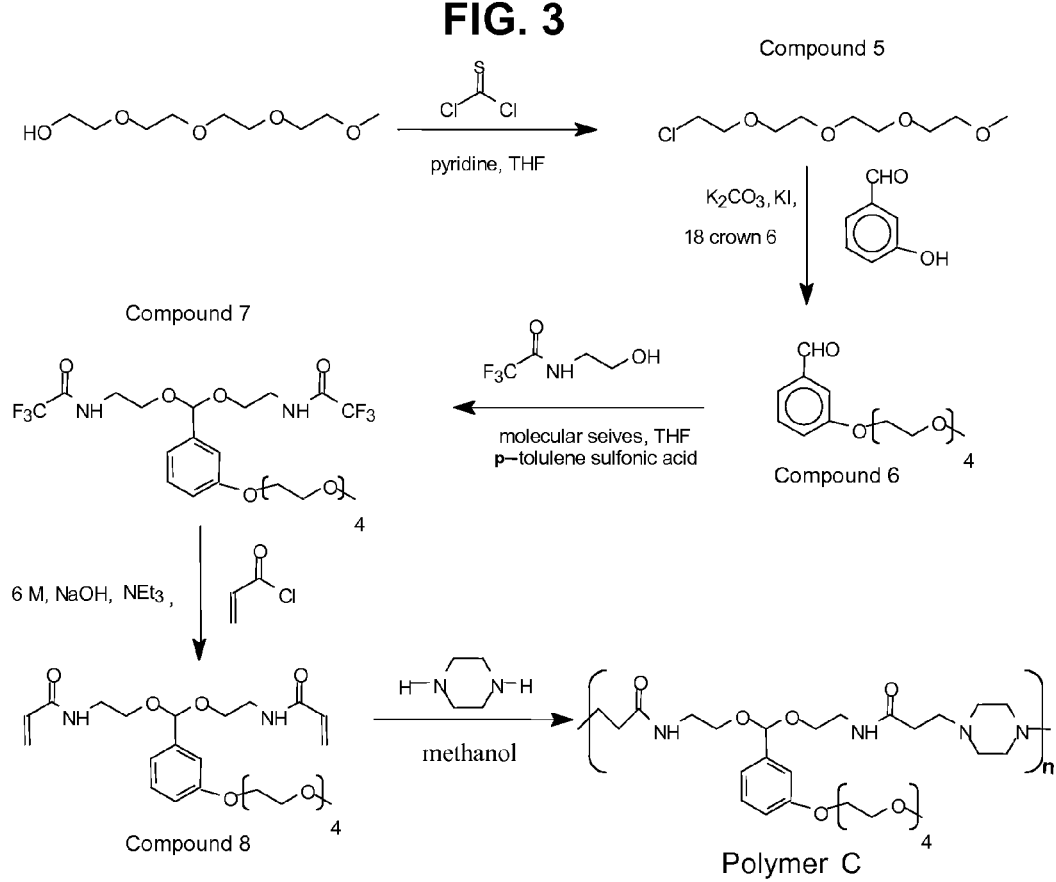
FIG. 3 shows an overall synthetic scheme for the preparation of Polymer C.

A group of three poly (amidoamines) structures (FIG. 1) were selected and synthesized with different acid sensitive linkages. The overall synthetic schemes for the preparation of Polymer A, B and C is given in FIG. 2 and FIG. 3.

Design and Synthesis of the Monomers: Bisacrylamide monomers (3, 4) with different acetal linkage were synthesized in two steps. Reaction of N-(2-hydroxyethyl)-phthalimide (2 equiv) was carried out either with acetaldehyde dimethyl acetal or dimethoxy propane in dry benzene with constant distillation in the presence of a catalytic amount of p-Toluenesulphonic acid. The intermediate was then deprotected with 6 M NaOH, and the product was allowed to react with acryloyl chloride to afford desired compound (3, 4).

General Procedures and Materials: All reagents were purchased from chemical suppliers and used without further purification unless otherwise noted. Tetrahydrofuran (THF) was distilled under nitrogen from Na/benzophenone prior to use. p-Toluenesulphonic acid was dehydrated and then recrystallized from toluene. N-(2-hydroxyethyl)-(2,2,2-trifluoroacetamide) and acryloyl chloride were freshly distilled before use. After extractive workup, organic layers were combined and dried with anhydrous $MgSO_4$. To avoid hydrolysis of acid sensitive compounds during chromatography separation on Merck Kieselgel 60 silica gel (230-400 mesh), Monomer 8, based on the benzaldehyde acetal, was synthesized in four different steps. Compound 5 was synthesized according to the procedure reported by Loth and Ulrich in *Controlled Release*. 1998; 54:273-282, and was then used to alkylate, 3-hydroxybenzaldehyde using potassium carbonate as the base and 18-crown-6 as the phase transfer catalyst to afford compound 6. Compound 6 was converted into acetal 7 by reaction with N-(2-hydroxyethyl)-2,2,2-trifluoroacetamide in the presence of catalytic amount of p-Toluenesulphonic acid in dry THF as a solvent. The final bisacrylamide monomer 8 was obtained by cleaving the trifluoroacetyl groups on compound 7 in 6 M NaOH/dioxane followed by reaction of the resulting diamine with an excess amount of acryloyl chloride.

Synthesis of Compound 1. N-(2-hydroxyethyl)-phthalimide (5 g, 26.15 mmol, 2 equiv) was dissolved in 100 mL of benzene, followed by addition of dimethoxy propane (1.36 g, 13.07 mmol, 1 equiv) and p-Toluenesulphonic acid (0.15 g, 2.6 mmol, 0.1 equiv). The reaction mixture was stirred with constant distillation of benzene at 94° C. for 3-4 h. The reaction mixture was quenched with triethylamine (1 mL) and the excess residual benzene was removed under reduced pressure. The crude product was purified by silica gel column chromatography using 4/1 hexane/ethyl acetate, 1/1 hexane/ ethyl acetate and finally ethyl acetate alone as the eluent. The product (4.2 g, 9.92 mmol, 42% yield) was obtained as a white solid. Mp: 143-144.2° C. IR (cm$^{-1}$): 1396 (s), 1708 (s), 3458 (br, m). $^1$H NMR (300 MHz, CDCl$_3$): δ1.25 (s, 6 H), 3.59 (t, 2 H, J=12.3), 3.81 (t, 2 H, J=13.2), 7.67 (m, 4 H, J=8.4), 7.81 (m, 4 H, J=8.7). $^{13}$C NMR (CDCl$_3$) δ 24.68, 38.12, 57.95, 123.26, 132.11, 133.88, 168.18. Calcd: [M+H]$^+$ (C$_{23}$H$_{25}$N$_2$O$_6$) m/z=423.44. Found FAB-HRMS: [M+H]$^+$= 423.4398.

Anal. Calcd: C, 64.07; H, 5.87; N, 6.79. Found C, 64.43; H, 5.98; N, 6.68.

Synthesis of Compound 2. This compound was prepared according to the reaction conditions reported for the synthesis of compound 1 except for the use of acetaldehyde dimethyl acetal instead of dimethoxy propane. The product was purified by silica gel column chromatography using 4/1 hexane/ ethyl acetate, 1/1 hexane/ethyl acetate and finally ethyl acetate alone as the eluent. The product (4.8 g, 11.7 mmol, 46% yield) was obtained as a white solid. Mp: 133.2-134° C. IR (cm$^{-1}$): 1394 (s), 1711 (s), 3469 (br, m). $^1$H NMR (400 MHz, CDCl$_3$): δ1.2 (d, 3 H, J=5.6), 3.63-3.90 (m, 8 H), 4.7 (q, 1 H, J=16), 7.7 (dd, 4 H, J=8.4), 7.81 (m, 4 H, J=8.2). $^{13}$C NMR (CDCl$_3$) δ 19.28, 37.71, 61.42, 99.03, 123.26, 132.06, 133.93, 168.17. Calcd: [M+H]$^+$ (C$_{22}$H$_{21}$N$_2$O$_6$) m/z=409.364. Found FAB-HRMS: [M+H]$^+$=409.3651. Anal. Calcd: C, 64.7; H, 4.94; N, 6.86. Found C, 64.49; H, 4.91; N, 6.89.

Synthesis of Compound 3. Compound 1 (4 g, 9.44 mmol, 1 equiv) and 6 M NaOH (16 mL) were combined and the reaction mixture was refluxed overnight at 105° C. followed by addition of dioxane (20 mL) after cooling. Upon complete removal of the acetamide groups, as determined by TLC using ninhydrin staining, the reaction mixture was cooled to 0° C. Acryloyl chloride (1.5 g, 9.44 mmol, 1 equiv) and triethylamine (5.73 g, 56.64 mmol, 6 equiv) were added in a small alternating portions with constant monitoring of pH. A 10% K$_2$CO$_3$ in water solution was added and the reaction mixture was stirred for 10 min and the product was extracted with six 100 mL portions of ethyl acetate. The organic layer was dried and the crude mixture was purified by silica gel column chromatography with 1/1 hexane/ethyl acetate and finally with 100% ethyl acetate to get (1.5 g, 5.54 mmol, 61% yield) white solid. Mp: 72-72.8° C. IR (cm$^{-1}$): 1059 (s), 1556 (s), 1657 (s), 3400 (br, m). $^1$H NMR (400 MHz, CDCl$_3$): δ1.3 (s, 6 H), 3.52-3.57 (m, 8 H), 5.68 (dd, 2 H, J=11.6, J=1.6), 6.15 (m, 2 H, J=2), 6.32 (dd, 2 H, J=18.4, J=1.6). $^{13}$CNMR (CDCl$_3$) δ 24.74, 39.69, 59.11, 100.12, 126.58, 130.65, 166.0. Calcd: [M+H]$^+$ (C$_{13}$H$_{23}$N$_2$O$_6$) m/z=271.348. Found FAB-HRMS: [M+H]$^+$=271.346. Anal. Calcd: C, 57.76; H, 8.20; N, 10.36. Found C, 56.89; H, 8.24; N, 10.34.

Synthesis of Compound 4. The experimental procedure for the synthesis of compound 4 is same as for the synthesis of compound 3 except compound 2 was used in place of compound 1. The product was purified by silica gel column chromatography using 1/1 hexane/ethyl acetate and finally with 100% ethyl acetate to get white solid (1.1 g, 55% yield). Mp: 70-71.4° C. IR (cm$^{-1}$): 1137 (s), 1556 (s), 1659 (s), 3429 (br, m). $^1$H NMR (400 MHz, CDCl$_3$): δ1.28 (d, 2 H, J=5.4), 3.47-3.68 (m, 8 H), 5.5 (q, 1 H, J=12), 5.6 (dd, 2 H, J=13.5, J=1.8), 6.09 (m, 2 H) 6.26 (dd, 2H, J=18.6, J=2). $^{13}$C NMR (CDCl$_3$) δ 19.49, 39.59, 63.79, 100.12, 126.43, 130.75, 166.04. Calcd: [M+H]$^+$ (C$_{12}$H$_{21}$N$_2$O$_6$) m/z=257.294. Found FAB-HRMS: [M+H]$^+$=257.2942. Anal. Calcd: C, 56.24; H, 7.87; N, 10.93. Found C, 55.99; H, 7.98; N, 10.87.

Synthesis of Compound 5. This compound was prepared according to the procedure reported by Loth and Ulrich (Controlled Release. 1998; 54:273-282). The product was isolated by short path distillation (106° C./2 mm Hg). IR (cm$^{-1}$): 1149 (s), 2875 (s). $^1$H NMR (400 MHz, CDCl$_3$): δ3.37 (s, 3H), 3.55 (t, 2H, J=4.8) 3.61-3.69 (m, 12H), 3.73 (t, 2H, J=5.7). $^{13}$C NMR (CDCl$_3$) δ 42.60, 58.61, 67.34, 67.44, 69.31, 70.32, 70.75, 71.07, 71.67. Calcd: [M+H]$^+$ (C$_9$H$_{20}$O$_4$Cl) m/z=227.96. Found FAB-HRMS: [M+H]$^+$= 227.965. Anal. Calcd: C, 47.68; H, 8.45. Found C, 47.42; H, 8.60.

Synthesis of Compound 6. Chloride 5 (10 g, 44 mmol, 1.3 equiv) and m-hydroxybenzaldehyde (4.2 g, 34 mmol, 1 equiv) were dissolved in dry THF (20 mL). K$_2$CO$_3$ (4.6 g, 34 mmol, 1 equiv) was added followed by 18-crown-6 (1.01 g, 3.74 mmol, 0.11 equiv). The reaction mixture was stirred at reflux for 48 h. The resulting mixture was cooled to rt and water (100 mL) was added. The product was extracted with 4×150 mL portions of ethyl acetate and the organic layers were combined and dried. The oil was loaded onto a silica gel column and eluted with 1/9 ethyl acetate/hexane, 1/4, 3/7, 4/1 ethyl acetate/hexane and finally with ethyl acetate alone to afford yellow oil as product (8 g, 75%). IR (cm$^{-1}$): 2874 (b), 1697 (s), 1109 (s). $^1$H NMR (300 MHz, CDCl$_3$): δ3.36 (s, 3 H), 3.54 (t, 2 H, J=4.8) 3.61-3.73 (m, 10 H), 3.75 (t, 2 H, J=4.8), 4.12 (t, 2 H, J=5.2), 7.1 (m, 3 H,), 7.25 (m, 1 H), 9.85 (s, 1 H). $^{13}$C NMR (CDCl$_3$) δ 42.60, 58.61, 67.34, 67.44, 69.31, 70.32, 70.75, 71.07, 71.67, 114.82, 121.57, 123.05, 129.15, 137.62, 159.20, 190.78. Calcd: [M+H] (C$_{16}$H$_{25}$O$_6$) m/z=313.1651. Found FAB-HRMS: [M+H]$^+$=313.1632. Anal. Calcd: C, 61.52; H, 7.74.

Found C, 60.98; H, 7.32.

Synthesis of Compound 7. Aldehyde 6 (2 g, 6.4 mmol, 1 equiv) and N-(2-hydroxyethyl)-2,2,2-trifluoroacetamide (7.37 g, 44.8 mmol, 7 equiv) were dissolved in dry THF (30 mL) followed by addition of p-Toluenesulphonic acid (0.21 g, 1.24 mmol, 0.16 equiv) and 5 Å molecular sieves (30 g). The reaction mixture was stirred overnight and quenched with triethylamine the next day. Molecular sieves from the reaction mixture were removed by filtering with a buckner funnel. A 150 mL portion of water was added to the filtrate and the reaction mixture was extracted with 5×150 mL portion of ethyl acetate. The ethyl acetate was evaporated and the yellow oil was loaded onto the silica gel column. The product was purified by eluting the column with 2/1 hexane/ethyl acetate, 1/1 hexane/ethyl acetate, 1/2 hexane/ethyl acetate and finally with ethyl acetate alone to afford light yellow colored solid. The product was recrystallized twice from ethyl acetate/hexane (1.9 g, 48% yield). Mp: 87.5-88.9° C. IR (cm$^{-1}$): 3306 (b), 2886 (s), 1714 (s), 1564 (s), 1157 (s). $^1$H NMR (300 MHz, CDCl$_3$): δ3.34 (s, 3 H), 3.36-3.65 (m, 8 H), 3.71-3.84-3.73 (m, 12 H), 3.79 (t, 2 H, J=4.8), 4.09 (t, 2 H, J=5.2), 5.49 (s, 1 H), 7.1 (m, 3 H,), 7.25 (m, 1 H), 9.85 (s, 1 H). $^{13}$C NMR (CDCl$_3$) δ 42.60, 56.12, 61.34, 64.44, 69.31, 70.32, 70.75, 71.07, 71.67, 100.57, 114.82, 117.81, 121.57, 123.05, 129.15, 137.62, 156.40 (q, J=35), 164.2 (s). Calcd: [M+H]$^+$ (C$_{24}$H$_{35}$O$_9$F$_6$N$_2$) m/z=609.224. Found FAB-HRMS: [M+H]$^+$=609.2246. Anal. Calcd: C, 47.37; H, 5.63; N, 4.60. Found C, 47.68; H, 5.32; N, 4.53.

Synthesis of Compound 8. Compound 7 (1.5 g, 2.46 mmol 1 equiv) and 6 M NaOH (20 mL) were added to dioxane (10 mL) and the reaction mixture was stirred at rt for 4 h. Complete removal of the acetamide groups was determined by TLC using ninhydrin staining. Upon completion, the reaction mixture was cooled to 0° C. Acryloyl chloride (1.3 g, 14.7 mmol, 6 equiv) and triethylamine (4.3 g, 44.3 mmol, 18 equiv) were added in small portions with constant monitoring of pH to maintain it above 7. A 10% $K_2CO_3$ in water solution was added and the reaction mixture was stirred for 10 minutes and the product was extracted with 6×100 mL portions of ethyl acetate. The organic layer was dried and crude was purified by silica gel column chromatography with 1/1 hexane/ethyl acetate and finally with 100% ethyl acetate to get product, yielding 0.8 g of product (61%). IR (cm$^{-1}$): 3350 (b), 1659 (s), 1556 (s), 1102 (s). $^1$H NMR (400 MHz, DMSO-d$_6$): δ3.17 (s, 3 H), 3.29-3.55 (m, 20 H), 3.72 (t, 2 H, J=4.8), 4.06 (t, 2 H, J=4.4), 5.52 (s, 1 H), 5.55 (dd. 2 H, J=12, J=2), 6.10 (dd, 2H, J=16, J=2), 6.21 (dd, 2 H, J=9), 6.89 (d, 1 H, J=9), 6.98 (d, 1 H, J=8.4), 7.21 (t, 1 H,), 8.23 (s, 2 H). $^{13}$C NMR (CDCl$_3$) δ 42.60, 56.12, 61.35, 64.44, 69.36, 70.34, 70.73, 71.09, 71.5, 100.68, 114.82, 117.86, 121.43, 123.06, 130.78, 131.63, 137.62, 159.20, 165.2 (s). Calcd: [M]$^+$ ($C_{26}H_{40}O_9N_2$) m/z=524.2733. Found FAB-HRMS: [M+H]$^+$=525.2812. Anal. Calcd: C, 59.5; H, 7.69; N, 5.34. Found C, 59.54; H, 7.89; N, 5.21.

Benzaldehyde acetals are well suited because their acid liability can be manipulated by the introduction of substituents at different positions of the aromatic ring. The introduction of an electron donating methoxy group at the meta position decreases the rate of hydrolysis of the acetal relative to the unsubstituted benzaldehyde or para and ortho substituted benzaldehyde. It was also necessary to introduce a hydrophilic moiety to the benzene ring to increase hydrophilicity and solubility in protic solvents. Therefore, the tetraglyme monomethyl ether was introduced at the meta position. This modification not only decreased the rate of hydrolysis of the benzaldehyde acetal dramatically but also improved the solubility of monomer 8 in protic solvents.

Polymer Synthesis Poly (amidoamines) are synthetic polymers obtained by stepwise polyaddition of primary or secondary aliphatic amines to bisacrylamide. Three acid degradable polyamidoamines polymers were prepared containing different acetal or ketal linkages. The rate of hydrolysis of the acetal linkages selected for Polymer A, B and C varies from 0.248, 7.52×10$^2$ and 8.15 respectively; in 50% dioxane and 50% water mixture. The reason for selecting these specific acetal linkages is to prepare polymers with different rate of hydrolysis. The polymerization was carried out as reported in the literature using an equimolar ratio of bisacrylamide monomers and piperazine in a protic solvent, either water or methanol, and the polymer were isolated by the precipitation with acetone (See Wan, K.; Malgesini, B.; Verpilio, I.; Ferruti, P.; Griffiths, P. C.; Paul, A.; Hann, A. C.; Duncan, R., Biomacromolecules 2004, 5, 1102-1109; Wang, D.; Liu, Y.; Hu, Z.; Hong, C.; Pan, C., Polymer 2005, 46, 3507-3514; and Dey, R. K.; Ray, A. R.; J Macromol Sci Pure and Appl Chem 2005, 42, 351-364). Aprotic solvents, even if highly polar such as, DMSO, were unsuitable as reaction media as they yielded only low molecular weight products. Relatively large-scale reactions were conducted to avoid any weighing error. Since this type, of polymerization is based on step growth polyaddition it is very important all the monomers are highly pure, otherwise it may cause a stoichiometric imbalance. Polymerization of degradable bisacrylamide monomers 3, 4 with piperazine was performed using water as a solvent. Due to the partial solubility of compound 8 in water, methanol was used as a solvent to carry out polymerization.

Synthesis of Polymer A, B and C. The Michael addition polymerization of degradable bisacrylamide monomers (compound 3 or 4) with an equimolar piperazine was performed using water pH 7 as a solvent. Compound 3 (1.02 g, 3.7 mmol) or compound 4 (1.08 g, 3.7 mmol) was reacted with piperazine (0.31 g, 3.7 mmol) in 2 mL of distilled water. Due to the partial solubility of monomer 8 (2.09 g, 3.8 mmol) in water, methanol was used as the solvent. To a stirred solution of bisacrylamide in water, piperazine was added and nitrogen was flushed through the reaction mixture for 10 min. The temperature of the polymerization mixture was kept at 50° C. and the reaction mixture was stirred for 7-8 h. The polymer was isolated by the precipitation with acetone. 1% triethylamine was added to the solvents used for elution.

Characterization. $^1$H NMR spectra were recorded at 300 or 400 MHz and $^{13}$C spectra were recorded at 100 MHz. NMR chemical shifts are reported in ppm relative to tetramethylsilane (TMS) and calibrated against residual solvent peaks: CDCl$_3$ (δ 7.26, δ 77.23) or DMSO-d$_6$ (δ2.44, δ 39.51) or D$_2$O (δ4.6). All coupling constants are reported in Hz. High resolution fast bombardment mass spectrometry (FAB-HRMS) experiments were performed at UC Berkeley mass spectrophotometry facility. Fourier transform Spectroscopy (FTIR) was done using thin film cast from $CH_2Cl_2$ on a refractive mirror surface. Elemental analyses were performed at the UC Berkeley analytical facility. Gel permeation chromatography (GPC) was carried out on a Waters 410 (refractive index) apparatus with two columns in a series TSK-GEL (2500 PW×1)+TSK-GEL (3000 PW×1) using 0.1 M tris/0.1 M LiBr solution in distilled water as eluent and poly(ethylene glycol) standards.

Characterization of Polymer A: IR (cm$^{-1}$): 1644 (s), 3409 (br, m). $^1$H NMR (500 MHz, DMSO-d$_6$): δ1.78 (d, 3 H, J=5), 2.188 (t (br), 4 H), 2.436 (t (br), 4 H), 3.16 (d, 4 H, J=5), 3.460 (d, 4 H, J=9.5) 4.648 (q, 1 H), 8.032 (s, 2 H). $^{13}$C NMR (DMSO-d$_6$) δ 19.67, 30.5, 39.2, 52.8, 54.6, 64.8, 100.5, 171.8.

Characterization of Polymer B: IR (cm$^{-1}$): 1640 (s), 3409 (br, m). $^1$H NMR (400 MHz, DMSO-d$_6$): δ1.29 (s, 6 H), 2.34 (t (br), 4 H), 2.65 (t (br), 4 H), 3.2 (d, 4 H, J=10.8), 3.45 (d, 4 H, J=9.5). $^{13}$C NMR (DMSO-d$_6$) δ 22.4, 32.6, 39.5, 51.8, 53.2, 59.8, 100.5, 172.8.

Characterization of Polymer C: IR (cm$^{-1}$): 1394 (s), 1709 (s), 3469 (br, m). $^1$H NMR (500 MHz, DMSO-d$_6$): δ 2.18 (t (br), 4 H), 2.4 (t (br), 4 H), 3.2 (s, 3 H), 3.35-3.76 (m, 16 H), 3.71 (s, 2 H), 4.05 (s, 2 H), 5.4 (s, 1 H), 6.89 (d, 1 H), 6.9 (d, 1 H), 7.2 (s, 1 H), 8.09 (s, 1 H). $^{13}$C NMR (DMSO-d$_6$) δ 33.4, 33.7, 38.90, 54.2, 54.8, 52.84, 58.44, 69.34, 69.97, 70.17, 70.22, 70.37, 71.64, 45.60, 100.80, 114.82, 113.72, 119.8, 130.6, 140.8, 159.38, 171.9.

Figure 4:
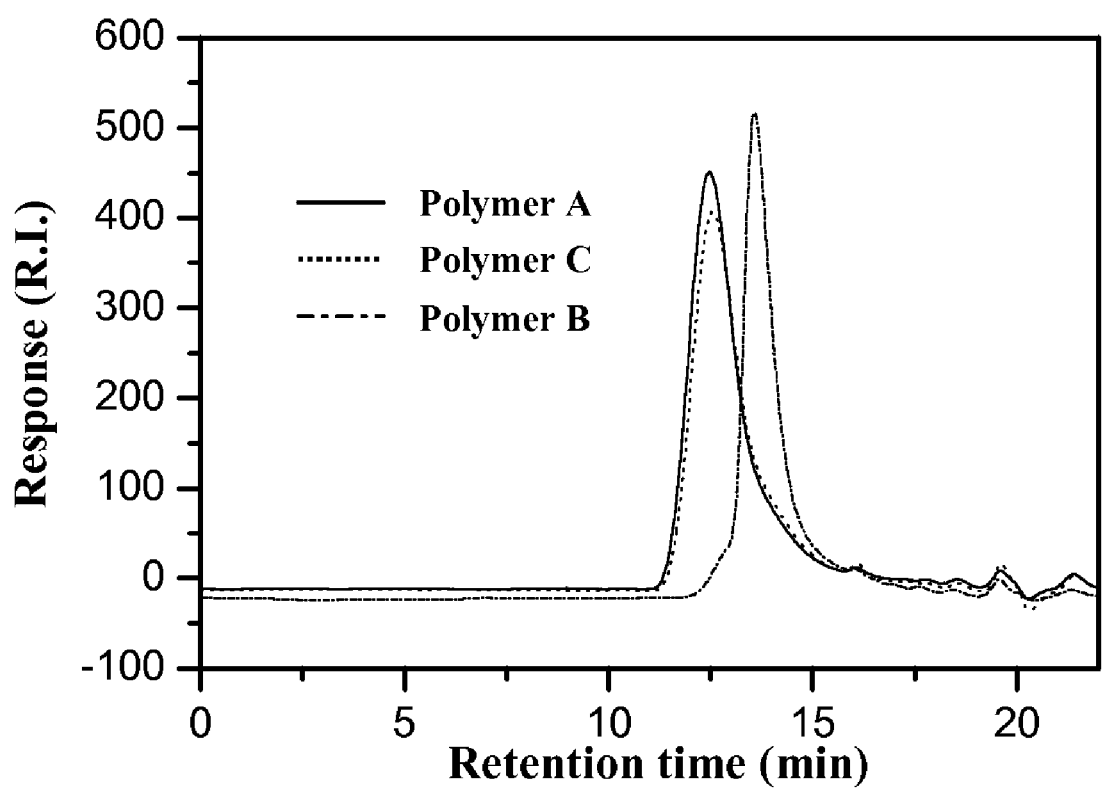
FIG. 4 shows a graph with superimposed GPC traces for Polymer A, B and C response over retention time to determine molecular weight.
Figure 5:
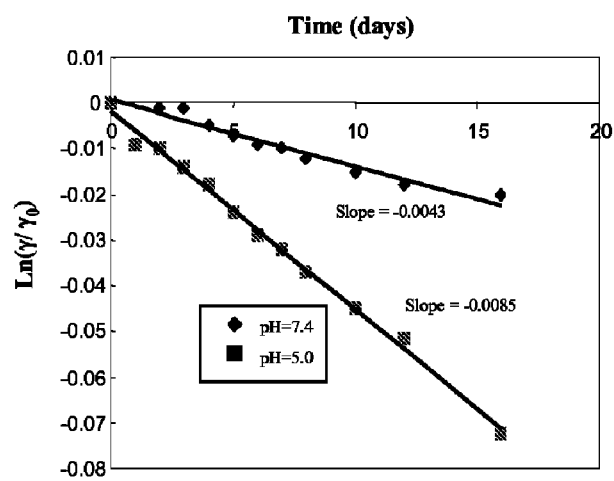
FIG. 5 is a graph showing the hydrolysis kinetics of Polymer A at pH 5.0 and 7.4.
Figure 6:
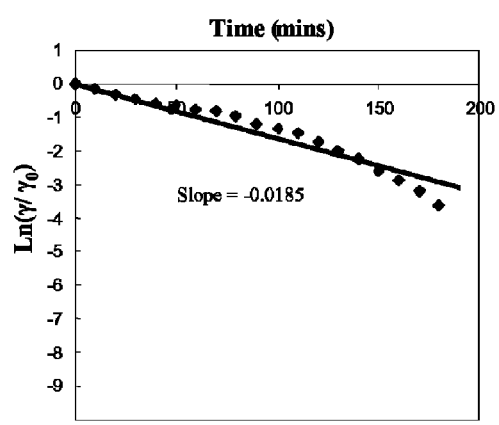
FIG. 6 is a graph showing the hydrolysis kinetics of Polymer B at pH 5.0.
Figure 7:
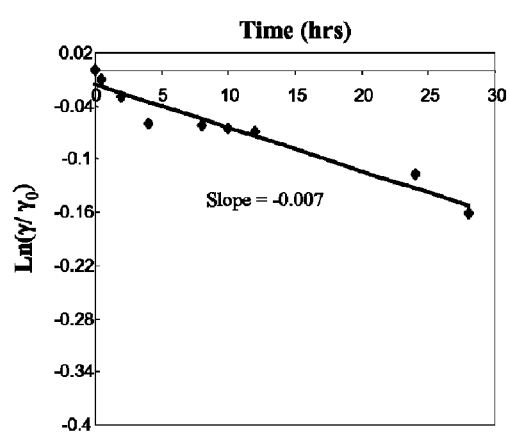
FIG. 7 is a graph showing the hydrolysis kinetics of Polymer B at pH 7.4.
Figure 8:
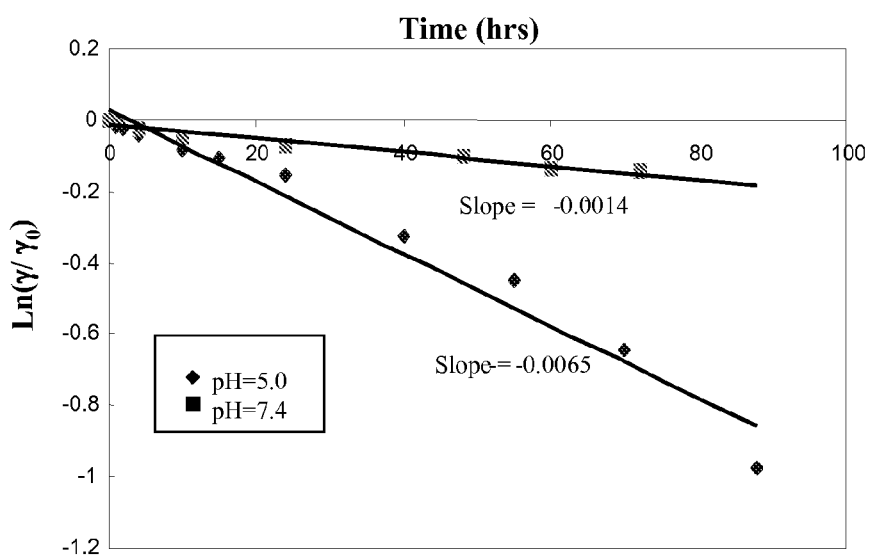
FIG. 8 is a graph showing the hydrolysis kinetics of Polymer C at pH 5.0 and 7.4.

The molecular weight (Mw) of each polymer, as measured by size exclusion chromatography (SEC), is given in Table 2 and FIG. 4. An aqueous pH 10 SEC setup was used to avoid the degradation of polymer during molecular weight measurement. The Mw of the polymer varied from 6491 D to 18790 D and the polydispersity index for all the polymers were in the range of 1.9-2.1.

TABLE 2

Molecular weight and polydispersity index of Polymer A, B and C

| Polymer | Mn (Da) | Mw (Da) | PDI |
| --- | --- | --- | --- |
| A | 9789 | 18790 | 1.91 |
| B | 3261 | 6491 | 1.99 |
| C | 6407 | 13456 | 2.1 |

SEC in water with 0.1 M Tris and 0.1 M LiBr with PEO Standards

A relatively high polydispersity index was obtained, which is common for step growth polymerization. The variation in the molecular weight of the polymers is most likely due to the difference in the rate of hydrolysis of acetal linkages. As mentioned earlier, this polymerization is well suited only in protic solvents, which may promote the degradation of acetal linkage present within the polymer backbone. We suspect the acetals underwent hydrolysis, especially in the case of Polymer B, which contains the most acid sensitive linkage leading to low molecular weight.

Degradation of the acetal during polymerization not only causes scission along the polymer backbone but also leads to monomer degradation resulting in the imbalance of stoichiometric ratio. Even if a small amount of acetal were degraded it would form byproducts that could cap the end of growing polymer chains leading to low molecular weight.

The Michael addition polymerization was carried out with commercially available non-degradable N,N-methylene-bis-acrylamide and piperazine using the same polymerization conditions. The molecular weight obtained with non-degradable bisacrylamide monomer was 52,402 D (data not shown). This also suggested the lower molecular weight, which we obtained with degradable bisacrylamide monomers, is may be because of the degradation of the acetal linkage present in the backbone. Although, we have obtained low molecular weight polymers but this might be useful for the delivery of proteins because larger cationic macromolecules induces higher cytotoxicity than low molecular weight polymers.

Hydrolyses of Polymer A, B and C: The hydrolysis kinetics of the polymers were measured at pH values corresponding to lysosomes (pH 5.0) and the blood (pH 7.4) at 37° C. The hydrolysis rate constant and half-life of the polymers were calculated using the Arrhenius equation (i.e; first order decay). Exponential decay half-lives calculated for Polymer A, B and C are given in FIGS. 5-8 and Table 23.

TABLE 3

Half-lives of polymer at A, B, C at pH 5.0 and 7.4.

| Polymer | pH | Half-Life |
|---------|-----|-----------|
| A | 5.0 | 81.5 days |
|   | 7.4 | 161 days |
| B | 5.0 | 37 minutes |
|   | 7.4 | 4.1 days |
| C | 5.0 | 4.4 days |
|   | 7.4 | 20.6 days |

A stock solution of deuteriated phosphate buffer (D-PBS) was prepared by dissolving 0.03 M KCl, 0.02 M $KH_2PO_4$ and 1.4 M NaCl and 0.1 M $Na_2HPO_4 \cdot H_2O$ in deuterium oxide. Working D-PBS buffers with pH 5.0, 7.4 were then prepared by adjusting the pH with 6 M NaOH. Hydrolysis experiments were started by adding 1 mL of pH 5.0 and 7.4 D-PBS solutions in a 10 mg of the polymer with rapid stirring. The time t=0 was taken as 1 min after mixing. Aliquots (0.5 mL) of each of the hydrolysis solutions were transferred to a airtight sealed NMR tubes and the spectra were taken at different time intervals. 3-(trimethyl silyl) propionic-2,2,3,3,$d_4$, sodium salt (δ −0.114) was used as an internal standard. The ratio 7 of hydrolyzed polymer at time t was determined by comparing disappearance of the integrated $^1H$ NMR spectra of the methyl protons (δ 1.78, d, 3 H) or dimethyl protons (δ 1.27, s, 6 H) or benzilidine proton (δ 5.49, 1 H, s) for polymer A, B and C, respectively, to the internal standard peak. The half-life of degradation was determined as $(\ln 2)/k_d$, where $k_d$ was a negative value of the slope obtained by plotting $\ln (\gamma/\gamma_0)$ versus incubation time t. The reference ratio of hydrolyzed to the total amount of crosslinker, $\gamma_0$, is the ratio at t=0 (1 min after mixing).

The rate of degradation of the polymers is in the order of Polymer B>C>A at both pH 5.0 and 7.4. The half-life of the polymer B is 170 times faster than polymer C, which is 19 times faster than polymer A at pH 5.0. Similarly at pH 7.4 polymer B degrades much faster than polymer A and C. The difference in the rate of degradation of Polymer A, B and C is due to the difference in the rate of hydrolysis of acetal linkage, which is present within the backbone of the polymeric chain. As expected, all polymers break down more quickly in mildly acidic environment (pH 5.0) than physiological pH 7.4. The acceleration of the hydrolysis kinetics of the polymer from 7.4 to pH 5.0 is expected because the rate of hydrolysis of acetal is proportional to the hydronium ion concentration, which increases 250 fold between 7.4 and pH 5.0. On the basis of these preliminary results, drug delivery systems prepared with the new acid degradable polyamidoamines may help control and accelerate release of therapeutic agents.

Thus, a series of different polyamidoamines that can degrade quickly in acidic medium but remain relatively stable in blood pH was shown to be successfully prepared. This new class of polymer is a promising material for drug delivery because of its ability to tune rate of degradation and high pH sensitivity. Therefore, future studies will focus on the application of these novel polymers as a carrier of therapeutic agents.

EXAMPLE 2

Synthesis of Acid Degradable Diamine, Isocyanate and Activated Diol Monomers

The first step in preparing the pH sensitive polyurea and polyurethanes was the synthesis of several functional monomers. Polyureas are commonly prepared via condensation of diamine and diisocyanate monomers. Therefore, a similar AA, BB system based on a diamine that contained dimethyl ketal to install acid sensitivity was designed. According to the literature, the hydrolysis half-life of a similar dimethyl ketal at pH 7.4 was 6 hours, but was 1.5 minutes at pH 5 demonstrating its pH dependent degradation kinetics (See Kwon, Y. J.; Standley, S.; Goodwin, A. P.; Gillies, E.; Frechet, J. M. J., Mol Pharm 2005, 2, 83-91.).

Figure 9:
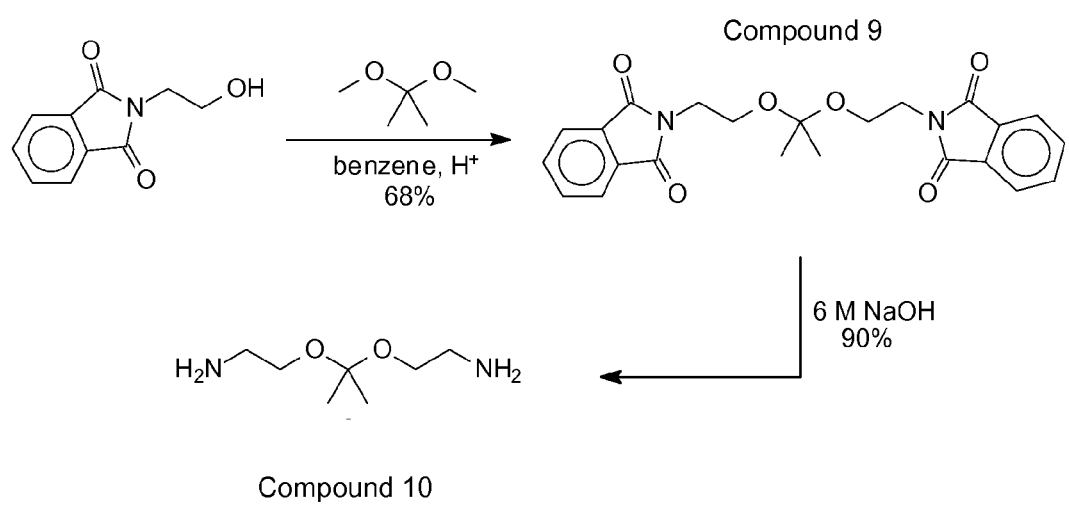
FIG. 9 is a scheme showing the synthesis of the acid degradable diamine monomer.

The acid degradable diamine monomer was synthesized in 2 steps by a procedure adapted from the literature (FIG. 9). First, an acetal exchange was performed using 1,2-dimethoxypropane and N-(2-hydroxyethyl)-pthalimide to prepare compound 9. To ensure the equilibrium shifted towards product formation, the methanol byproduct was removed from the system by an azeotropic distillation with benzene. Ketal 9 was then deprotected under strongly basic conditions to afford the target acid degradable diamine 10 in high yield.

General Procedures and Materials. Chemicals used for synthesis of monomers and polymers were obtained from Aldrich unless otherwise indicated. p-Toluenesulfonic acid was dehydrated by heating at 100° C. under vacuum for 6 h and then recrystallized from boiling toluene. Combined organic layers after extractions were dried over anhydrous $MgSO_4$. Solvents were removed under reduced pressure using a rotary evaporator. Merck Kieselgel plates coated with silica gel 60 $F_{254}$ were used for thin layer chromatography and were visualized by UV activity or ninhydrin staining. Flash column chromatography was performed with Merck Kieselgel 60 silica gel (230-400 mesh). When purifying acetal compounds, all flash column chromatography solvents contained 1-2% triethylamine. NMR chemical shifts are reported in ppm and are calibrated against residual solvent signals. All coupling constants are reported in Hz. FT-IR spectroscopic analyses were performed using a thin film from CH$_2$Cl$_2$ on a reflective mirror surface or using a KBr pellet. High resolution fast atom bombardment (FABHR-MS) experiments were performed at the UC Berkeley MS Facilities. Elemental analyses were performed by the UC Berkeley Microanalytical Laboratory. The size exclusion chromatography (SEC) system consisted of a Waters 510 pump, a manual Rheodyne 7161 injector and a Waters 410 refractive index detector. Analytical SEC in DMF containing 0.2% LiBr was performed at 70° C. at a flow rate of 1 mL/min on a chromatography line calibrated with poly(methylmethacrylate) standards (1280-910,500 g/mol) and fitted with two 75×300 mm PLgel columns (10$^3$ Å, 10$^5$ Å, 5 μm particle size). Polymer solutions (~1 mg/mL) were prepared and injected onto the system and monitored by refractive index detection.

Protected Diamine 9. N-(2-Hydroxyethyl)-pthalimide (5 g, 2 equiv., 26 mmol) was added to 200 mL benzene. Then a small portion of benzene (20 mL) was removed by distillation at 95° C. using a short path distillation head while stirring to remove water from the system. After cooling the flask to rt, 2,2-dimethoxypropane (1.6 mL, 1 equiv., 13 mmol) and p-toluenesulphonic acid (40 mg, 0.015 equiv, 0.23 mmol) were added. The benzene was then again removed by distillation in order to drive the reaction forward by removing methanol. Once distillation was complete, triethylamine (3.6 mL, 2 equiv., 26 mmol) was added to quench the acid. The reaction mixture was purified by column chromatography eluting with 50:50 hexanes/ethyl acetate to afford 9 as a white solid in 68% yield (7.5 g, 18 mmol). mp=149.9-152.6° C. IR (cm$^{-1}$): 1765 (m), 1702 (s), 1390 (m), 1367 (m), 1016 (m). $^1$H NMR (300 MHz, DMSO-d$_6$): δ 1.16 (s, 6), 3.41 (t, 4, J=6), 3.62 (t, 4, J=6), 7.77 (m, 8). $^{13}$C NMR (100 MHz, DMSO-d$_6$): δ 24.45, 37.58, 57.37, 99.93, 123.01, 131.41, 134.36, 167.61. Calcd: [M+H]$^+$ (C$_{23}$H$_{23}$N$_2$O$_6$) m/z=423.155. Found: FAB-HRMS: [M+H]$^+$m/z=423.156. Anal. Calcd. For C$_{23}$H$_{22}$N$_2$O$_6$: C, 65.40; H, 5.25; N, 6.63 Found: C, 65.38; H, 5.36; N, 6.61.

Acid-Degradable Diamine 10. Compound 9 (11.7 g, 27 mmol) was dissolved in 6 M NaOH (75 mL) was heated at reflux with stirring overnight. After cooling to rt, the product was extracted into 3:1 CHCl$_3$/isopropanol. The organic phase was dried with Mg$_2$SO$_4$ and solvent was removed in vacuo to afford 10 (4.0 g, 25 mmol) as a yellow oil in 90% yield. IR (cm$^{-1}$): 3372 (br), 1568 (s), 1480 (s), 1380 (m), 1314 (m), 1209 (m), 1155 (m), 1077 (m), 1031 (m). $^1$H NMR (300 MHz, DMSO-d$_6$): δ 1.25 (s, 6), 1.33 (br s, 4), 2.60 (t, 4, J=6), 3.29 (t, 4, J=6). $^{13}$C NMR (100 MHz, DMSO-d$_6$): δ 24.85, 41.81, 62.87, 99.01. Calcd: [M+H]$^+$ (C$_7$H$_{19}$N$_2$O$_2$) m/z=163.14465. Found: FAB-HRMS: [M+H]+m/z=163.14460.

Anal. Calcd. For C$_7$H$_{18}$N$_2$O$_2$: C, 51.83; H, 11.18; N, 17.27. Found: C, 51.70; H, 11.24; N, 17.33.

Figure 10:
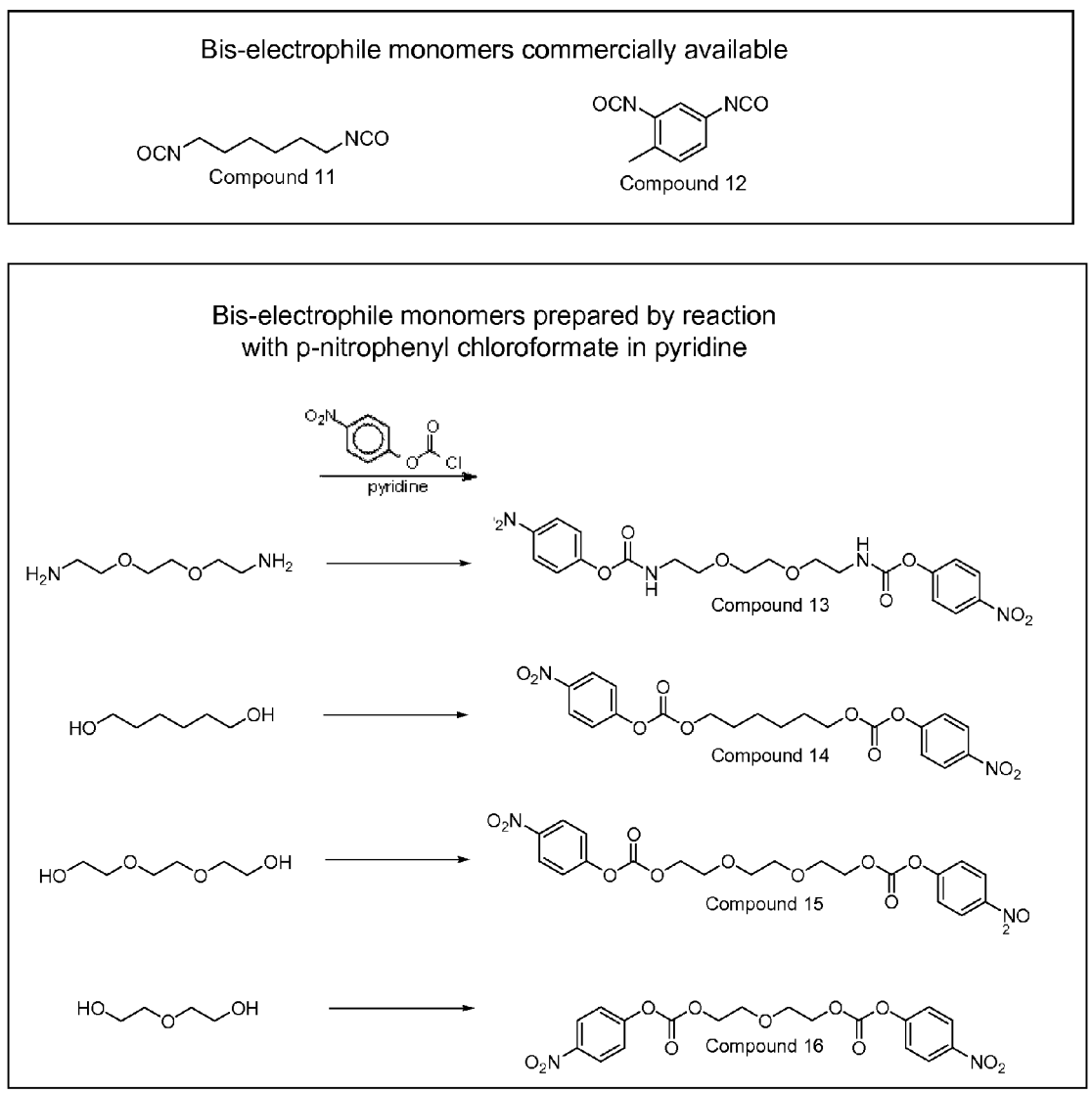
FIG. 10 shows the commercially obtained bis-eletrophile monomers and a synthesis scheme for diisocyanate and bis (p-nitrophenyl carbamate/carbonate) activated bis-electrophile monomers.

The diisocyanate monomers 11 and 12 were commercially available. Another type of monomer used for polyurea formation was a p-nitrophenyl carbonate activated diamine, 13, which was synthesized in 1 step (FIG. 10).

Bis(p-nitrophenyl carbamate) 13. 2,2'-(Ethylenedioxy)bis (ethylamine) (1.00 g, 1 equiv., 6.75 mmol) and pyridine (2.18 mL, 5 equiv., 27.0 mmol) were dissolved in CH$_2$Cl$_2$ (250 mL). The reaction flask was cooled to 0° C. and then p-nitrophenyl chloroformate (5.44 g, 4 equiv., 27.0 mmol) was added. The solution warmed to room temperature while stirring for 24 h. The reaction was filtered and the solvent was evaporated leaving a white solid. The crude product was dissolved in CH$_2$Cl$_2$ (150 mL) and washed with 1 M NaHSO$_4$ (3×30 mL). The organic layer was dried with MgSO$_4$ and the solvent was evaporated. The resulting solid was crystallized twice from CH$_2$Cl$_2$/hexanes providing 13 as a white solid in 68% yield (2.19 g, 4.58 mmol). The $^1$H NMR spectrum indicated that at rt a 4:1 ratio of conformational isomers were present. mp=134-137° C. IR (cm$^{-1}$): 3329 (s), 1715 (s), 1539 (s). $^1$H NMR (400 MHz, CDCl3): δ 3.52 (dt, J, =J$_2$=5 Hz, 3.2H, —CH$_2$NH—), 3.59 (dt, J, =J$_2$=5 Hz, 0.8H, —CH$_2$NH—), 3.68 (t, J=5 Hz, 4H, —OCH$_2$CH$_2$NH—), 3.71 (s, 4H, —OCH$_2$CH$_2$O—), 5.68 (br, 1.6H, NH), 5.90 (br, 0.2H, NH), 6.35 (br, 0.2H, NH), 7.30 (d, J=9 Hz, 4H, Ar—H), 8.23 (d, J=9 Hz, Ar—H). $^{13}$C NMR (125 MHz, CDCl$_3$): δ 40.98, 69.54, 70.22, 121.88, 125.00, 144.60, 153.10, 155.77. FAB-MS m/z: [M+H]$^+$ 479. Anal. Calcd. For C$_{20}$H$_{22}$N$_4$O$_{10}$: C, 50.21; H, 4.64; N, 11.71. Found: C, 49.93; H, 4.59; N, 11.46. In a similar fashion, several diols were also activated using p-nitrophenyl chloroformate to give monomers 14, 15 and 16 in good yields (FIG. 10). This series of monomers was synthesized for condensation with degradable diamine 10 to prepare acid sensitive polyurethanes.

Bis(p-nitrophenyl carbonate) 14. 1,6-hexanediol (2 g, 1 equiv., 17 mmol) was dissolved in dry CH$_2$Cl$_2$ (80 mL) followed by the addition of pyridine (6.9 mL, 5 equiv., 85 mmol). The reaction flask was cooled to 0° C. and then p-nitrophenyl chloroformate (8.6 g, 2.5 equiv., 43 mmol) was added. The solution stirred overnight while warming to rt. The reaction was washed with pH 4 buffer solution and then the organic phase was dried with Mg$_2$SO$_4$. The product was purified by column chromatography eluting with 80:20 hexanes/ethyl acetate. The product required further recrystallization using ethyl acetate/hexanes. 12 was isolated as a white solid in 59% yield (4.5 g, 10 mmol). mp=112.5-113.0° C. IR (cm$^{-1}$): 1764 (s), 1526 (s), 1347 (m), 1254 (s), 1213 (s). $^1$H NMR (300 MHz, DMSO-d$_6$): δ 1.40 (m, 4), 1.70 (m, 4), 4.25 (t, 4, J=6.5), 7.54 (d, 4, J=9), 8.30 (d, 4, J=9).

$^{13}$C NMR (100 MHz, DMSO-d$_6$): δ24.68, 27.73, 69.00, 122.57, 125.53, 145.09, 152.04, 155.28. Calcd: [M+H]$^+$ (C$_{20}$H$_{21}$N$_2$O$_{10}$) m/z=449.119. Found: FAB-HRMS: [M+H]$^+$ m/z=449.118. Anal. Calcd. For C$_{20}$H$_{20}$N$_2$O$_{10}$: C, 53.57; H, 4.50; N, 6.25. Found: C, 53.52; H, 4.43; N, 6.08.

Bis(p-nitrophenyl carbonate) 15 and 16. These compounds were prepared according to literature procedure (Yeager, A. R.; Finney, N. S. *J. Org. Chem.* 2004, 69, 613-618) and corresponded with the reported spectroscopic data.

All monomers had to be free of water and other impurities in order to reduce weighing error. This is particularly important when performing an AA, BB type step polymerization where the exact equal molar ratio is necessary to prepare high molecular weight polymers.

EXAMPLE 3

Synthesis of Acid-Degradable Polyurea and Polyurethane Polymers

Figure 11:
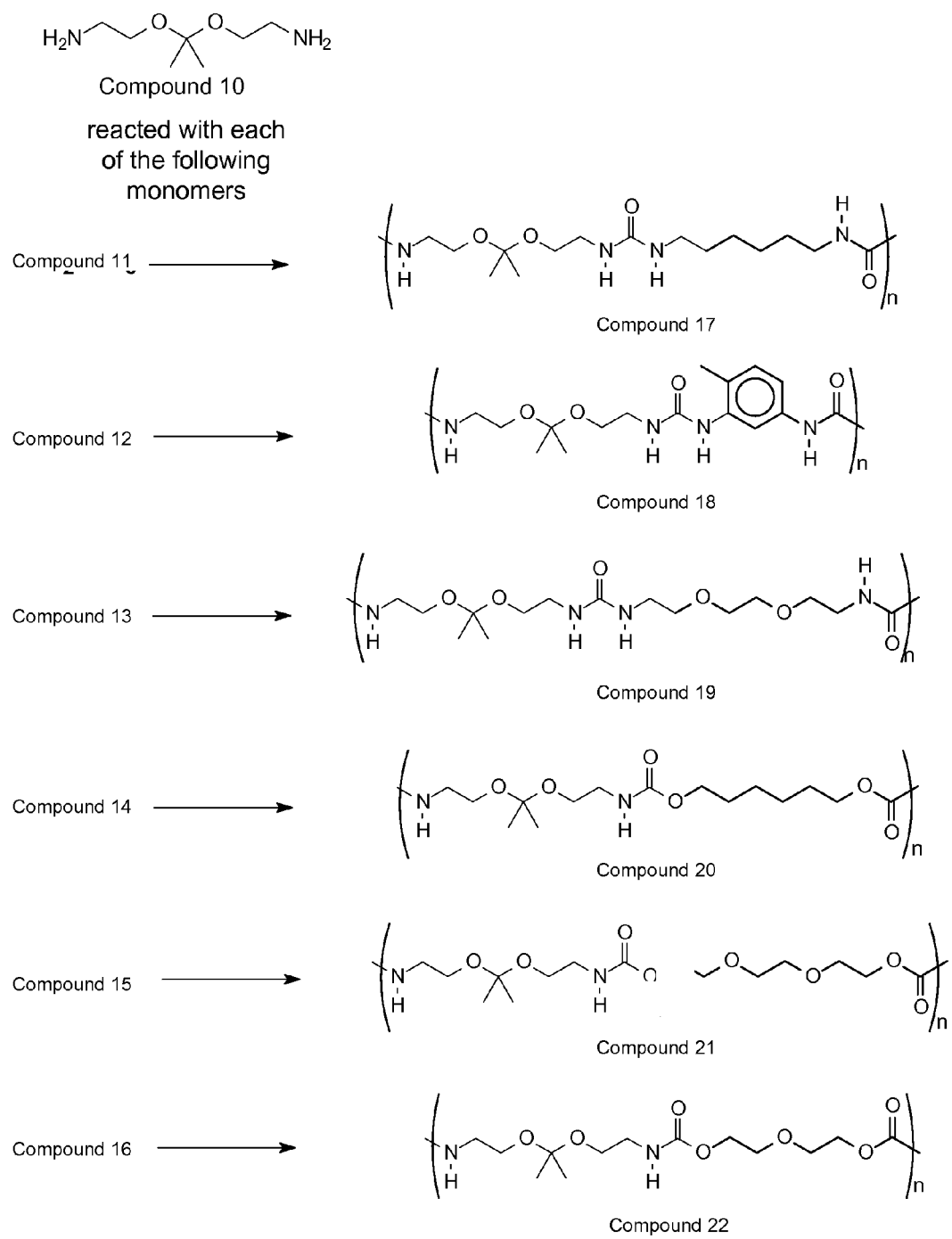
FIG. 11 shows the synthesis of polyureas and polyurethanes by the interfacial polymerization of degradable diamine monomer and diisocyanate and bis(p-nitrophenyl carbamate/carbonate) activated monomers.

Polyureas 17, 18 and 19 were formed by the interfacial step polymerization of degradable diamine 10 and monomers 11, 12, or 13. FIG. 11 shows the resulting polymers. The diamine was solubilized in water and then added to the diisocyanate or activated diamine monomer dissolved in dichloromethane. The resulting polymers precipitated from the reaction solution and the powder was isolated by filtration in high yields.

Preparation of Acid Degradable Polyureas 17, 18, 19. Compound 10 (0.102 g, 1 equiv., 0.63 mmol) was dissolved in CH$_2$Cl$_2$ (5 mL). To this solution aqueous buffer (5 mL, 30 mM phosphate, pH 8) and triethylamine (9 μL, 0.1 equiv., 0.06 mmol) were added and the mixture was stirred rapidly to form an emulsion. A solution of freshly distilled diisocyanate 11 or 12 (105 μL, 1 equiv., 0.65 mol) in CH$_2$Cl$_2$ (5 mL) was then added in one portion to the stirred emulsion, and stirring was continued at rt for 16 h. The precipitated polymer was filtered, washed with $CH_2Cl_2$, and dried in vacuo. The polymers were obtained with yields of 80-90%.

Polyurea 17. Polymer 17 was sparingly soluble in typical laboratory solvents, which precluded $^{13}C$ NMR and SEC analyses. IR ($cm^{-1}$): 3335 (br), 2934, (s), 1624 (s), 1585 (s). $^1H$ NMR (500 MHz, DMSO-$d_6$): δ 1.1-1.4 (br, 14H, —$CH_3$ and —$CH_2CH_2CH_2$—), 2.9-3.2 (br, 8H, —$CH_2NH$—), 3.3-3.4 (overlaps with water peak, —$CH_2O$—), 5.8-6.0 (br, 2H, NH), 6.0-6.2 (br, 2H, NH). Anal. Calcd. For $C_{15}H_{30}N_4O_4$: C, 54.53; H, 9.15; N, 16.96. Found: C, 54.17; H, 9.31; N, 16.66.

Polyurea 18. $^1H$-$^{13}C$ HMQC NMR was utilized to distinguish between NH and Ar—H resonances. IR ($cm^{-1}$): 3331 (br), 2934, (s), 1644 (s), 1554 (s). $^1H$ NMR (400 MHz, DMSO-$d_6$): δ 1.30 (s, 6H, —$CH_3$), 1.9-2.2 (s, 3H, Ar—$CH_3$), 3.21 (br, 4H, —$CH_2NH$—), 3.41 (br, 4H, —$CH_2NH$—), 6.03 (br, 1H, NH), 6.5-6.7 (br, 1H, NH) 6.85-7.0 (br, 1H, Ar—H), 7.10 (br, 1H Ar—H), 7.64 (br, 1H, NH), 7.69 (br, 1H, Ar—H), 8.44 (br, 1H, NH). $^{13}C$ NMR (125 MHz, DMSO-$d_6$): δ 17.24, 24.76, 24.79, 39.76, 39.92, 59.98, 99.63, 110.27, 111.65, 119.43, 129.95, 138.07, 138.46, 155.22, 155.34. Anal. Calcd. For $C_{16}H_{24}N_4O_4$: C, 57.13; H, 7.19; N, 16.66. Found: C, 56.74; H, 7.30; N, 16.35. SEC: $M_n$ 41.9 kDa, M, =83.5 kDa, PDI=1.99

Polymer 19. Polyurea 19 and polyurethanes 20-22 were prepared by step-growth polymerization of degradable diamine 10 and the activated monomers 13-16. All monomers were solubilized in dichloromethane, with a weak base (triethylamine) added in order to prevent hydrolysis of the ketals. Polymer 19 was isolated by precipitation from hexanes/isopropanol. Polymers 20-22 were not easily purified by precipitation; therefore, they were purified by dialysis against a methanol/triethylamine solution to remove thep-nitrophenol byproduct. Polymer 20 was a powder but 21 and 22 were sticky solids. The yields for the polyurethanes were lower than those for the polyureas most likely due to loss of low molecular weight material during dialysis.

Polyurethanes 20, 21 and 22 were prepared by step polymerization of degradable diamine 10 and the activated diols 14, 15 and 16. All monomers were solubilized in dichloromethane and a weak base, triethylamine, was added to prevent hydrolysis of the ketals. These polymers did not precipitate; therefore, they were purified by dialysis in a methanol/triethylamine solution to remove the p-nitrophenol byproduct. Polymer 18 was a powder but 21 and 22 were sticky solids. The yields for the polyurethanes were lower than those for the polyureas most likely due to loss of material during dialysis.

Preparation of Acid-Degradable Polyurea Polymer 19. Compound 10 (0.108 g, 1 equiv., 0.067 mmol) and $NEt_3$ (186 μL, 2 equiv., 1.33 mmol) were dissolved in $CH_2Cl_2$ (1.3 mL). To this solution was added solid 5 (0.318 g, 1 equiv., 0.067 mmol) in one portion. After stirring overnight, the viscous yellow solution was added to an excess of 1:1 isopropanol: hexanes to yield the product as a pale yellow solid in 66% yield (0.160 g, 0.044 mmol). IR ($cm^{-1}$): 3346 (br), 2869, (br), 1632 (s). $^1H$ NMR (400 MHz, DMSO-$d_6$): δ 1.25 (s, 6H), 3.15-3.2 (m, 8H), 3.25-3.4 (m, 8H), 3.50 (s, 4H), 5.98 (t, 2H, J=5), 6.05 (t, 2H, J=5).

$^{13}C$ NMR (100 MHz, DMSO-$d_6$): δ 25.17, 39.65, 40.09, 60.42, 70.03, 70.61, 99.85, 158.53. Anal. Calcd. For $C_{15}H_{30}N_4O_6$: C, 49.71; H, 8.34; N, 15.46. Found: C, 49.93; H, 8.56; N, 15.13. SEC: $M_n$ 16.5 kDa, $M_w$=39.9 kDa, PDI=2.42.

Polyurethanes 20, 21 and 22 were prepared by step polymerization of degradable diamine 10 and the activated diols 14, 15 and 16. All monomers were solubilized in dichloromethane and a weak base, triethylamine, was added to prevent hydrolysis of the ketals. These polymers did not precipitate; therefore, they were purified by dialysis in a methanol/triethylamine solution to remove the p-nitrophenol byproduct. Polymer 18 was a powder but 21 and 22 were sticky solids. The yields for the polyurethanes were lower than those for the polyureas most likely due to loss of material during dialysis.

Preparation of Acid Degradable Polyurethanes 20, 21, 22. Compound 10 (100 mg, 1 equiv., 0.62 mmol) was dissolved in dry $CH_2Cl_2$ (0.5 mL) along with dry triethylamine 215 μL, 2.5 equiv. 1.5 mmol). In as separate flask, either compound 6, 7, or 8 (1 equiv., 0.62 mmol) was dissolved in dry $CH_2Cl_2$ (0.5 mL). The two solutions were combined and stirred at rt for 2 d. The solution was then dialyzed using 3500 Mw cutoff regenerated cellulose tubing (Amersham) in MeOH/3% triethylamine. The solvent was then removed in vacuo and the polymers were dried. They were isolated in 50-80% yields.

Polyurethane Polymer 20. IR ($cm^{-1}$): 3325 (br), 1692 (s), 1535 (s), 1258 (s), 1155 (m). $^1H$ NMR (300 MHz, $CDCl_3$): δ 1.35 (m, 10), 1.61 (m, 4), 3.31 (m, 4), 3.46 (t, 4, J=5.3), 4.04 (t, 4, J=6.5), 5.12 (br s, 2). $^{13}C$ NMR (100 MHz, $CDCl_3$): δ 25.00, 25.73, 29.11, 41.24, 60.12, 65.01, 100.39, 156.97. Anal. Calcd. For $C_{15}H_{28}N_2O_6$: C, 54.20; H, 8.49; N, 8.43. Found: C, 54.26; H, 8.68; N, 8.34.

Polyurethane Polymer 21. IR ($cm^{-1}$): 3334 (br), 1703 (s), 1536 (s), 1257 (s). $^1H$ NMR (400 MHz, DMSO-$d_6$): δ 1.23 (s, 6), 3.06 (m, 4), 3.34 (m, 4), 3.51 (m, 8), 4.02 (m, 4), 7.16 (br s, 2). $^{13}C$ NMR (100 MHz, DMSO-$d_6$): δ 24.60, 40.55, 59.05, 63.07, 68.84, 69.65, 99.51, 156.19. Anal. Calcd. For $C_{15}H_{28}N_2O_8$: C, 49.44; H, 7.74; N, 7.69. Found: C, 49.37; H, 7.99; N, 7.44.

Polyurethane Polymer 22. IR ($cm^{-1}$): 3335 (br), 1707 (s), 1536 (s), 1257 (s) 1156 (s) 1057 (m). $^1H$ NMR (300 MHz, $CDCl_3$): δ 1.32 (s, 6), 3.31 (m, 4), 3.46 (t, 4, J=5), 3.68 (m, 8), 5.34 (br s, 2). $^{13}C$ NMR (100 MHz, $CDCl_3$): δ 25.01, 41.30, 60.03, 64.08, 69.71, 100.40, 156.62. Anal. Calcd. For $C_{26}H_{50}N_4O_{15}$ ($C_{13}H_{24}N_2O_7$+0.5$H_2O$): C, 47.41; H, 7.65; N, 8.51. Found: C, 47.23; H, 7.55; N, 8.29.

A variety of polymer structures were prepared. All polymerizations were similar in that an exact 1:1 ratio of monomers was necessary to afford high molecular weights. The structures were also similar in that they contained the same acid sensitive dimethyl ketal linkage embedded in the backbone. The structures differed in that some contained hydrophobic hexyl chains, such as 17 and 20 whereas others had hydrophilic ethylene oxide units, such as 19, 21 and 22. Polymer 18 contained an asymmetric aromatic ring. They also differed in the fact that the polyureas had ureas in each repeat unit, whereas the polyurethanes had carbamates.

These structural differences were expected to affect their solubilities. Polyurethanes 20, 21 and 22 easily dissolved in polar organic solvents, such as DMSO and dichloromethane, but were not completely soluble in water. Polyureas 17, 18 and 19 were less water soluble than the polyurethanes and were more difficult to dissolve in organic solvents. Polymer 9 was never completely solubilized in the organic solvents unlike, 18 and 19. In general, the polyureas were less soluble than the urethane counterparts most likely due to strong hydrogen bonding interactions between polymer chains. The other observed trend was that more hydrophilicity in the polymer backbone lead to better solubility in polar solvents. Also, the asymmetry of polymer 18 may have helped increase its solubility.

EXAMPLE 4

Characterization of Acid-Degradable Polyurea and Polyurethane Polymers and their Degradation Products The molecular weight of the polymer was measured with a DMF SEC system using PMMA calibration standards. Weight average molecular weights of approximately 20 k-50 k and PDIs of 1.5-2.5 were achieved. The lower PDIs of the polyurethanes were most likely due to the removal of lower molecular weight fragments during purification by dialysis. NMR and elemental data corresponded with the expected polymer structures.

Size Exclusion Chromatography Characterization of Polymers. Polymers were dissolved in DMF (~1 mg/mL) containing 0.2% LiCl. They were injected onto an SEC system and elution was monitored by RI detection. Molecular weight was determined by comparison to a calibration curve of PMMA standards.

These polymers were designed to break down into small molecules upon a drop in pH. All polymers were expected to release acetone, which is nontoxic, and a diol after hydrolysis of the dimethyl ketal linkage. The expected diol degradation product for each polymer is shown in Table 1.

Isolation and Characterization of Degradation Products. 50 mg of each polymer was dissolved in 10 mL of millipore water and 2 drops of concentrated HCl were added. The polymer solutions stirred overnight at rt and then water was removed by lyophilization. The remaining white solids were characterized To confirm the structures of the degradation products, the polymers were incubated in acidic aqueous solution overnight and the resulting products were isolated via lyophilization. Mass spectroscopy and NMR data corresponded with the diol structures in Table 1. Acetone was not observed, although this was expected to evaporate during the lyophilization.

Degradation Product of Polymer 17. $^1$HNMR (300 MHz, DMSO-$d_6$): δ 1.1-1.4 (m, 8H, —$CH_2CH_2CH_2$—), 2.94 (t, J=7 Hz, 4H, —$CH_2NH$—), 3.02 (t, J=6 Hz, 4H, —$CH_2NH$—), 3.34 (t, J=6 Hz, 4H, —$CH_2O$—). $^{13}$C NMR (100 MHz, DMSO-$d_6$): δ 26.12, 29.98, 39.16, 42.07, 60.86, 158.28. FAB-MS m/z: [M+H]$^+$ 291.

Degradation Product of Polymer 18. $^1$H NMR (300 MHz, DMSO-$d_6$+DCl (cat.)): δ 1.9-2.2 (m, 3H), 3.07 (m, 4H), 3.36 (m, 4H), 6.7-7.2 (m, overlaps with water peak), 7.6-7.9 (m, 1H). $^{13}$C NMR (100 MHz, DMSO-$d_6$+DCl (cat.)): δ 18.14, 42.28, 42.43, 61.03, 112.17, 113.30, 121.62, 130.66, 138.50, 138.74, 156.51, 156.73. FAB-MS m/z: [M+Li]$^+$303.

Degradation Product of Polymer 19. $^1$H NMR (400 MHz, DMSO-$d_6$): δ 3.04 (m, 4H), 3.13 (m, 4H), 3.36 (m, 8H), 3.50 (s, 4H), 5.99 (br, 4H). $^{13}$C NMR (125 MHz, DMSO-$d_6$): δ 39.3 (shoulder on solvent peak), 42.13, 60.88, 69.65, 70.21, 158.33. FAB-MS m/z: [M+H]$^+$ 323. Anal. Calcd. For $C_{12}H_{26}N_4O_6$: C, 44.71; H, 8.13; N, 17.38 Found: C, 44.40; H, 8.25; N, 17.06.

Degradation Product of Polymer 20. The expected degradation product was obtained with a minor impurity (4%). The minor impurity is most likely a molecule derived from a p-nitrophenyl carbonate polymer chain end that had been converted to a methyl carbonate (singlet at 3.78 ppm) during dialysis in methanol. $^1$H NMR (300 MHz, CDCl$_3$): δ 1.39-1.41 (m, 4H), 1.63 (m, 4H), 3.34 (br, 4H), 3.72 (br, 4H), 4.08 (br, 4H), 5.20 (br s, 2H).

$^{13}$C NMR (100 MHz, DMSO-$d_6$): δ 25.13, 28.66, 42.97, 59.97, 63.57, 156.47. Calcd: [M+H]$^+$ ($C_{12}H_{25}N_2O_6$) m/z=293.1712. Found: FAB-HRMS: [M+H]$^+$m/z=293.1715.

Anal. Calcd. For $C_{12}H_{24}N_2O_6$: C, 49.30; H, 8.28; N, 9.58 Found: C, 49.07; H, 8.37; N, 9.20.

Degradation Product of Polymer 21. The expected degradation product was obtained with an impurity (12%). The impurity is most likely a molecule derived from a p-nitrophenyl carbonate polymer chain end that had been converted to a methyl carbonate (singlet at 3.78 ppm) during dialysis in methanol. $^1$H NMR (300 MHz, CDCl$_3$): δ 2.63 (br, 2H), 3.33 (br, 4H), 3.66 (s, 4H), 3.69-3.72 (m, 8H), 4.25 (br, 4H), 5.61 (br, 2H). $^{13}$C NMR (100 MHz, CDCl$_3$): δ 43.53, 61.92, 64.12, 69.59, 70.61, 157.13. Calcd: [M+Li]$^+$($C_{12}H_{24}N_2O_8$Li) m/z=331.1692. Found: FAB-HRMS: [M+Li]$^+$m/z=331.1699. Anal. Calcd. For $C_{12}H_{26}N_2O_9$ ($C_{12}H_{24}N_2O_8$+$H_2O$): C, 42.10; H, 7.65; N, 8.18 Found: C, 42.40; H, 7.78; N, 7.92.

Degradation Product of Polymer 22. $^1$H NMR (400 MHz, MeOD): δ 3.20 (t, 4H, J=6), 3.57 (t, 4H, J=6), 3.67 (t, 4H, J=5), 4.14 (t, 4H, J=5). $^{13}$C NMR (100 MHz, MeOD): δ 44.19, 61.90, 65.07, 70.50, 159.05. Calcd: [M+H]$^+$ ($C_{10}H_{21}N_2O_7$) m/z=281.134. Found: FAB-HRMS: [M+H]$^+$ m/z=281.135. Anal. Calcd. For $C_{10}H_{22}N_2O_8$ ($C_{10}H_{20}N_2O_7$+$H_2O$): C, 40.27; H, 7.43; N, 9.39 Found: C, 40.82; H, 7.33; N, 9.21.

EXAMPLE 5 pH Dependant Polyurea and Polyurethane Polymer Degradation Determined by Gas Chromatography A pH 7.4 buffer solution of 0.1 M $Na_2HPO_4$ in millipore water and a pH 5 buffer solution of 0.1 M acetic acid in millipore water were prepared. Both solution contained 1 μL/mL of the internal reference 1,2-dimethoxyethane. A DMSO solution containing 1 μL/mL of 1,2-dimethoxyethane was also prepared. Acetone calibration curves at both pH 7.4 and pH 5 were prepared using these solutions in a range of 0.039 to 5.0 μL/mL. The solution consisted of 10% DMSO and 90% buffer solution. Polymer degradation was monitored by dissolving 10 mg of each polymer in 100 μL of the DMSO solution in a GC vial. Then 900 μL of a pH 7.4 or pH 5 buffer solution was added at t=0. The vial was centrifuged and then 1 μL of the polymer solution was injected onto the GC column using an autosampler at t=5 minutes. The GC vial was then incubated at 37° C. with stirring between time points and the vial was centrifuged prior to each injection. Injections were also performed at t=0.5, 1, 2, 4, 24 and 48 h. The peak area ratio of acetone to dimethoxyethane was calculated and compared to the acetone calibration curve to determine % release of acetone for each time point. The concentration at which the acetone leveled off was taken to be the value for complete degradation.

To investigate the pH dependent hydrolysis kinetics, polymer degradation was monitored over time. The polymers were dissolved in either a pH 7.4 or pH 5 buffered aqueous solution containing 10% DMSO and incubated at 37° C. The concentration of acetone released into the solution was measured by GC at time points ranging from 5 minutes to 48 hours. Some of the polymer solutions were heterogenous due to their poor solubility. In these cases, the powdery solid was pelleted at the bottom of the GC vial by centrifugation before sampling. No heterogenous or homogenous system was found where all of the polymers behaved similarly due to their differences solubility.

Figure 13:
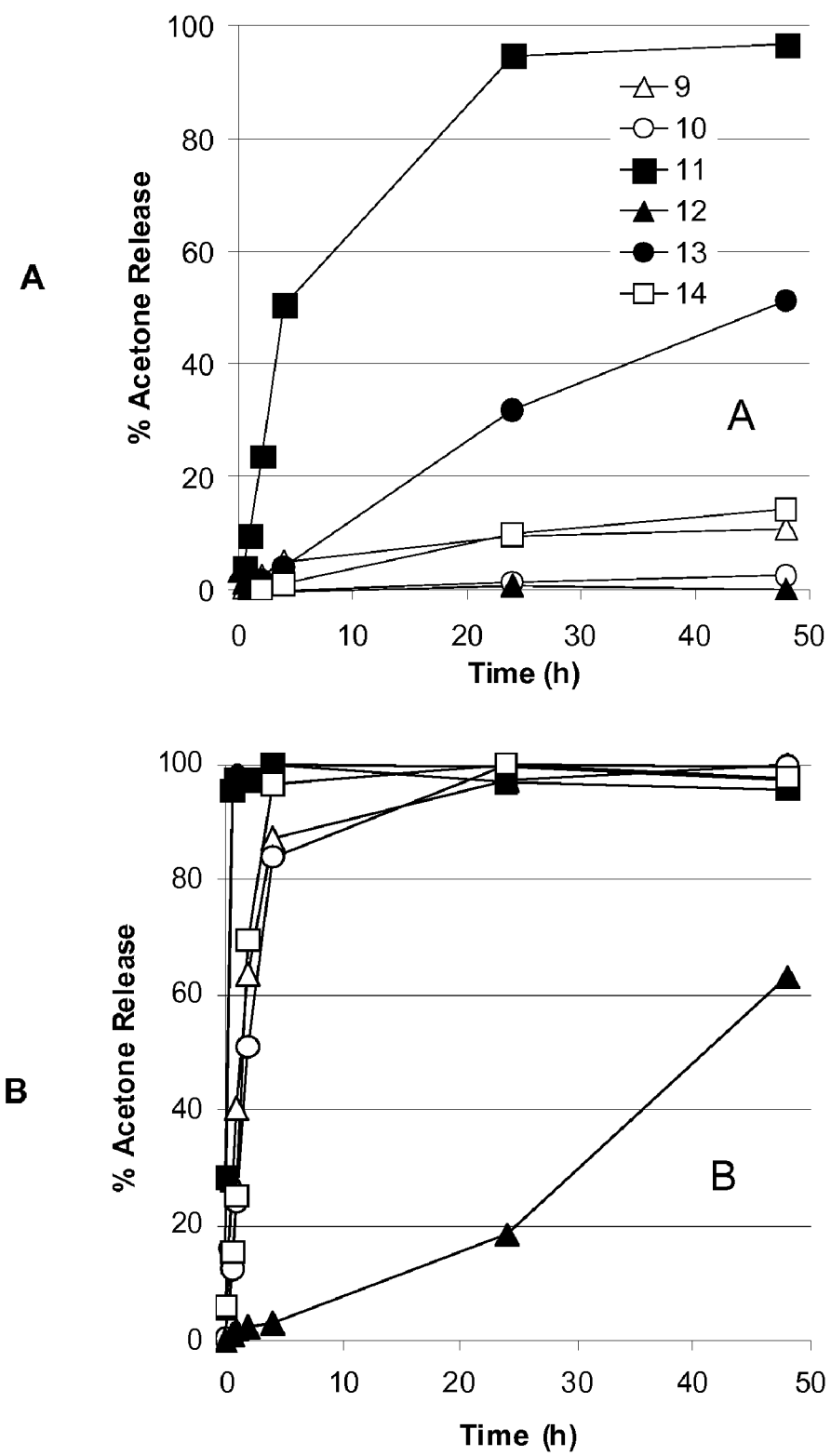
FIG. 13 is two graphs showing pH-dependant degradation of polymers at A) pH 7.4 and B) pH 5.0, by measuring the concentration of acetone released into the solution as measured by gas chromatography at time points ranging from 5 minutes to 48 hours.

All of the polymers demonstrated faster release of acetone at pH 5.0 compared to pH 7.4, as expected (FIG. 13). This pH dependence is consistent with the hydrolysis kinetics for the dimethyl ketal linkage incorporated into the polymer backbone. In general, the polyureas degraded faster than their polyurethane counterparts, probably due to their greater capability to hydrogen bond with water. It was also noted that the more hydrophilic ethylene oxide based polymers, such as 19, degraded faster than the aliphatic hydrocarbon-based polymers, such as 17, most likely due to their enhanced solubility in water. It is well established that for polymer erosion and degradation, the hydrophilicity and crystallinity of a material strongly influences its rate of hydrolysis. With the exception of 20, the polymers completely degraded into small molecules within one day at pH 5.0, with the more hydrophilic species fully degrading in a few hours. The acetone release profile of polymer 20 differed greatly from that of the other polymers because it behaved poorly in water, becoming a sticky solid that was not easily suspended during the degradation experiment. This probably resulted in a lower solvent-exposed surface area, which can slow hydrolysis. An initial induction period was observed followed by a period of faster polymer hydrolysis. One possible explanation for this result is that penetration of water into the surface layers of the polyurethane takes more time due to higher polymer hydrophobicity. Once an adequate amount of water has entered the polymer matrix, ketal hydrolysis can begin, resulting in hydrophilic hydroxy-containing species that can attract more water and accelerate the degradation process. This type of erosion behavior has been noted in the literature for poly (orthoesters). See Ng, S., Y.; Taylor, M., S.; Heller, J. *Macromolecules* 1997, 30, 770-772.

Polyureas and polyurethanes that degrade quickly in mildly acidic environments similar to those found in endosomes and tumor tissues, but are more stable at the physiological pH of 7.4 were successfully designed and synthesized. The ease of preparation, the ability to tune solubility, and the polymers' high pH-sensitivity identify this new class of polymers as promising materials for drug delivery systems. The bis-electrophiles utilized here represent only a fraction of the possible co-monomers that could be polymerized. These polymers could be used as the matrix for particulate delivery systems, or could be easily modified to covalently carry low molecular weight drugs and/or targeting molecules, making them attractive targets for use in biomaterials science.

EXAMPLE 7

Synthesis of Degradable Polymer Particles

In one embodiment, the polyurea and polyurethane polymers in the previous examples will be used to prepare acid-degradable protein-loaded particles for protein-based vaccines. In previous methods, the preparation of acid-degradable particles was performed by an inverse emulsion polymerization of acrylamide and pH-sensitive crosslinkers in the presence of protein (Standley, S. M.; Kwon, Y. J.; Murthy, N.; Kunisawa J.; Shastri, N.; Guillaudeu, S. J.; Lau, L.; Fréchet J. M. J. *Bioconjugate Chem.* 2004, 15, 1281-1288). In this method, the polymer network and particles are prepared in the same step. Other techniques, such as double emulsion and spray drying, afford protein-loaded particles where the polymer is synthesized or purchased first, followed by a second particle forming step (Liu, R.; Ma, G.; Meng, F.; Su, Z. *J. Controlled Release* 2005, 103, 31-43; Witschi, C.; Mrsny, J. R. *Pharm. Res.* 1999, 16, 382-390).

Figure 14:
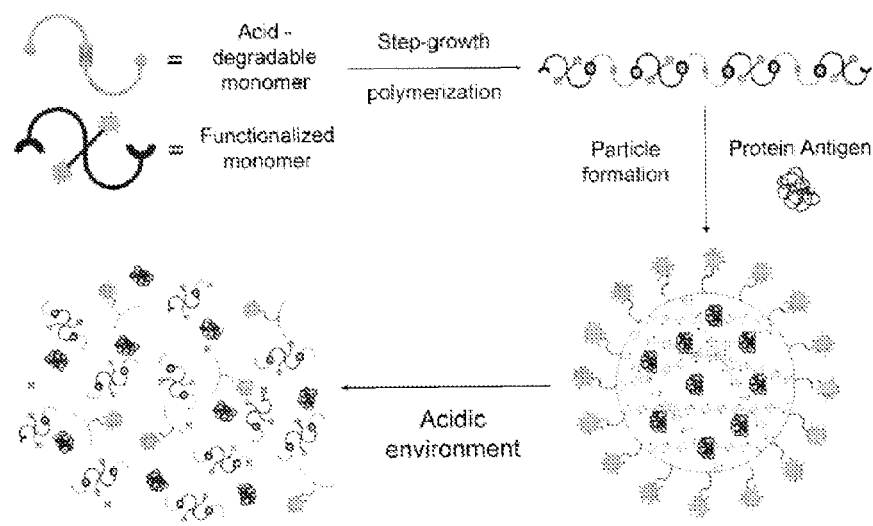
FIG. 14 is a cartoon showing the application of linear main chain acid-degradable polymers for protein-loaded particle preparation and expected particle response to an acidic environment.
Figure 15:
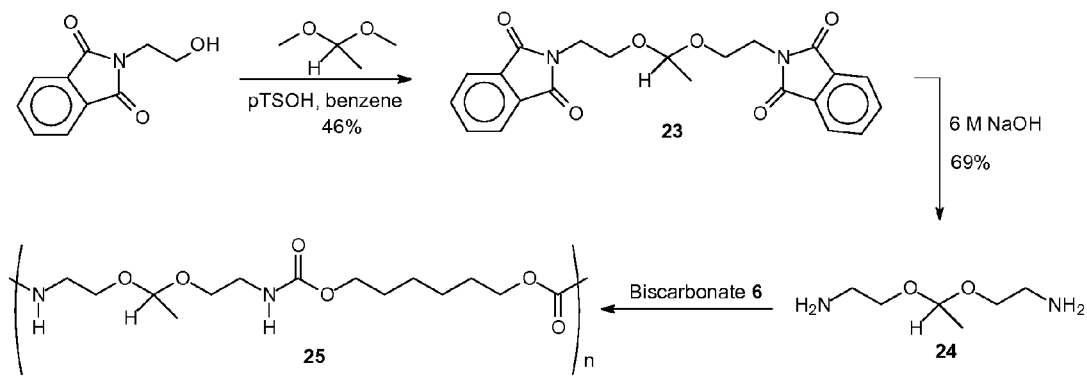
FIG. 15 is scheme showing the synthesis of degradable polyurethane 25 polymer particles using double emulsion polymerization.

An initial investigation into double emulsion particle preparation using polyurethane 17 was performed (FIG. 14). The polyurethane used in this experiment is a derivative of polymer 12, where the dimethyl ketal was exchanged for an acetaldehyde acetal. This acetal is much less sensitive to acid catalyzed hydrolysis, with the second order hydrolysis rate constant being three orders of magnitude lower than the dimethyl ketal. Using a polymer that is less susceptible to degradation under aqueous conditions was important to optimize the double emulsion procedure because the process involves contact of the polymer with water. If an acid-sensitive polymer was used and the procedure resulted in no particle formation, it would be unclear if this was due to improper processing conditions or due to polymer hydrolysis. Polyurethane 25 was synthesized using similar reactions conditions described for the preparation of polyurethanes 20, 21 and 22 (FIG. 15). First, the pthalimide-protected diamine monomer, 23, was prepared via an acetal exchange reaction followed by deprotection under strongly basic conditions to afford the new diamine monomer, 24. Biscarbonate monomer 14 was then copolymerized with diamine 24 to afford polyurethane 25, which contained the new acetaldehyde acetal linkage.

Protected Diamine 23. This compound was prepared according to the reaction conditions reported for the synthesis of compound 9 except for the use of acetaldehyde dimethyl acetal instead of 2,2-dimethoxypropane. The product was purified by silica gel column chromatography using 4:1 hexane/ethyl acetate, 1:1 hexane/ethyl acetate and finally ethyl acetate alone as the eluent. The product (4.8 g, 11.7 mmol, 46% yield) was obtained as a white solid. Mp: 133.2-134.0° C. IR (cm$^{-1}$): 3469 (br, m), 1711 (s), 1394 (s). $^1$H NMR (400 MHz, CDCl$_3$): δ 1.25 (d, 3, J=5), 3.36-3.92 (m, 8), 4.78 (q, 1, J=5), 7.11 (m, 4), 7.84 (m, 4). $^{13}$CNMR (CDCl$_3$): δ 19.28, 37.71, 61.42, 99.03, 123.26, 132.06, 133.93, 168.17. Calcd: [M+H]$^+$ (C$_{22}$H$_{21}$N$_2$O$_6$) m/z=409.364. Found FAB-HRMS: [M+H]$^+$=409.3651. Anal. Calcd: C, 64.70; H, 4.94; N, 6.86. Found: C, 64.49; H, 4.91; N, 6.89.

Diamine 24. This compound was prepared according to the reaction conditions reported for the synthesis of compound 10 except for the use of compound 23 instead of compound 9. The product was obtained as a yellow oil (0.50 g, 3.7 mmol, 69% yield). $^1$H NMR (300 MHz, DMSO-d$_6$): δ 1.18 (d, 3, J=5), 1.39 (br, 4), 2.62 (t, 4, J=6), 3.28-3.49 (m, 4), 4.78 (q, 1, J=5).

Polyurethane 25. Diamine 24 (0.05 g, 3.7 mmol, 1 equiv.) and dry triethylamine (1.8 mL, 8.5 mmol, 2.5 equiv.) were dissolved in dry CH$_2$Cl$_2$ (2.7 mL). In a separate flask, compound 14 (1.5 g, 3.7 mmol, 1 equiv.) was dissolved in CH$_2$Cl$_2$ (2.7 mL). The two solutions were combined and stirred at rt for 2 d. The polymer was then dialyzed against MeOH/1% triethylamine in 1 k MW cutoff regenerated cellulose tubing (Amersham). The solvent was removed in vacuo and the polymer was isolated as a white powder in 93% yield. $^1$H NMR (300 MHz, DMSO-d$_6$): δ 1.16 (br, 3), 1.29 (br, 4), 1.50 (br, 4), 3.09 (br, 4), 3.45 (br, 4), 3.90 (br, 4), 4.62 (br, 1), 7.07 (br, 2). SEC: M$_n$ 55.5 kDa, M$_w$=92.8 kDa, PDI=1.67.

Figure 17:
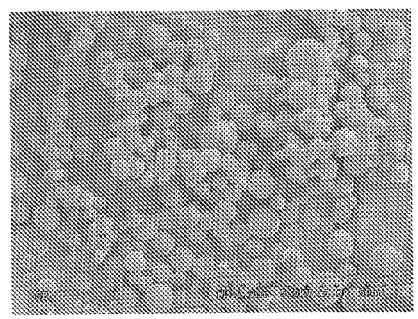
FIG. 17 is a micrograph showing the SEM image of particles made by double emulsion polymerization. Scale bar=50 μm
Figure 16:
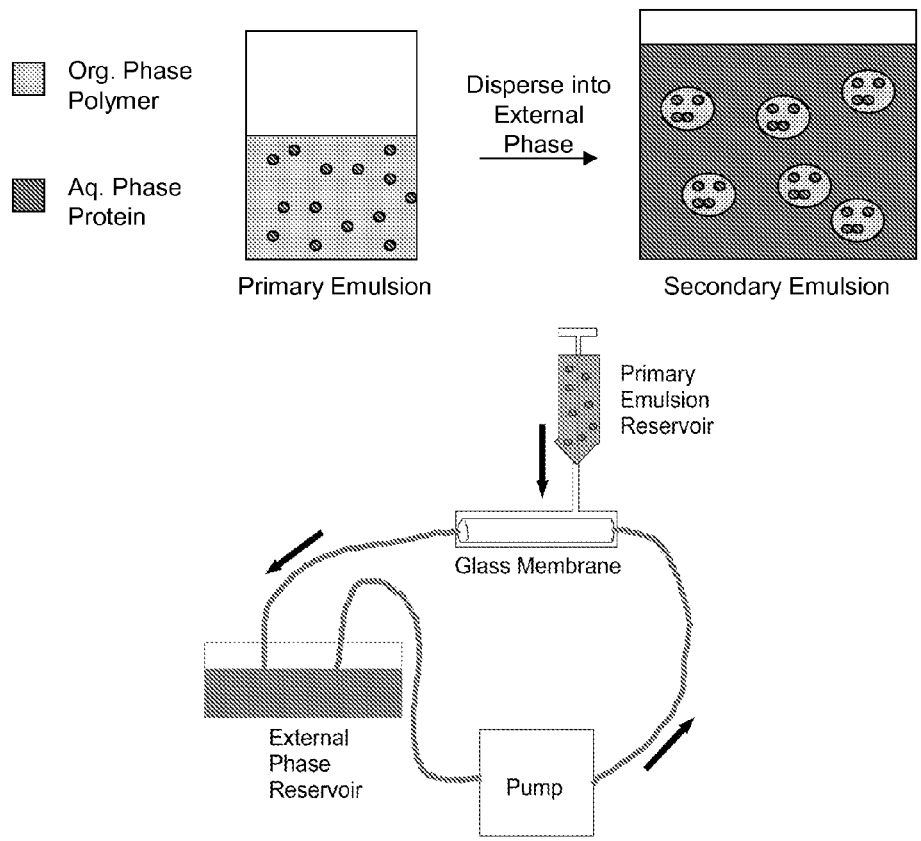
FIG. 16 shows the method and apparatus used for double emulsion polymerization.

This polymer was then used to form particles via double emulsion. First, the polymer was dissolved in dichloromethane along with the surfactant Arlacel 83. Then, a small amount of aqueous solution containing the protein, ovalbumin, was dispersed into the organic/polymer phase by sonication forming a water-in-oil emulsion (FIG. 16). This primary emulsion was then dispersed into a larger amount of pH 8 water containing a stabilizer, poly(vinyl alcohol), to form the secondary water-in-oil-in-water emulsion. This was done using the apparatus illustrated in FIG. 16. The primary emulsion was injected through a glass membrane of uniform pore sizes into the bulk external aqueous phase that was being cycled through the instrument by a magnetic gear pump. This technique has been described by Liu, R.; Ma, G.; Meng, F.; Su, Z. *J. Controlled Release* 2005, 103, 31-43, and is hereby incorporated by reference. After forming the secondary emulsion, the solution was stirred at rt for 4 h until the dichloromethane evaporated. When evaporated, the polymer collapsed around the aqueous protein solution forming protein-loaded particles that were isolated by centrifugation. A scanning electron microscopy image shows that particles of 2.5 to 8 µm were formed (FIG. 17). The size range, as discussed in earlier chapters, is well suited for particle vaccine applications. Future studies involve using these double emulsion conditions to prepare particles with the pH-sensitive polymers A, B, C, 17-22, and 25.

Double Emulsion Particle Formation. Three solutions were prepared: (1) Inner aqueous phase: 5 mg ovalbumin dissolved in 2.7 mL distilled water. (2) Oil phase: 0.45 g polyurethane 25 and 0.26 g Arlacel 83 dissolved in 9.60 mL $CH_2Cl_2$. (3) External aqueous phase: 1.8 g hydrolyzed poly(vinyl alcohol) (88% hydrolyzed, 100 k) dissolved in 180 mL pH 8 distilled water. Solution 1 was dispersed into solution 2 by sonication and then this primary emulsion was loaded into a 10 mL syringe. The external phase was added to the reservoir (see FIG. 16) and was cycled through the glass membrane by a magnet gear pump. The Shirasu porous glass membrane had a uniform pore size of 1.5 µm. The primary emulsion was injected across the glass membrane into the cycling external phase. The solution was collected in the external reservoir and stirred at rt for 4 h. The solution was centrifuged and the white solid pellet was isolated and washed with pH 8 water twice. Particles were imaged using a scanning electron microscope at 5 kV after drying and sputter coating with a 20 nm gold film.

EXAMPLE 8

Class I Antigen Presentation Assays

In one embodiment, particles prepared from these acid degradable epolymer backbones are designed to release their bioactive material payload into the cytoplasm of cells upon lysosomal destabilization. Higher loading capacity of the particles may also lead to greater antigen presentation of the encapsulated bioactive material. In the antigen presentation assay described by Sanderson, S.; Shastri, N. in *Inter. Immun.* 1994, 6, 369-376, the β-galactosidase activity of B3Z T cells is measured. Antigen presenting cells display the peptide having the sequence, SIINFEKL (SEQ ID NO: 8), upon phagocytosis of ovalbumin. These cells are engineered to transcribe β-galactosidase when in the presence of antigen presenting cells displaying the SIINFEKL peptide (SEQ ID NO: 8). β-galactosidase then liberates chlorophenol red from the chlorophenol red βgalactoside that is present in solution. Absorbance of chlorophenol red is measured by UV absorbance at 595 nm. Therefore this assay can be used as a measurement of the amount of bioactive material delivered into the cytoplasm of cells by the microgel particles of the invention by measuring the amount of liberated chlorophenol red by UV absorbance at 595 nm.

A proper control would be to compare the amount presented by the particles when incubated with the SIINFEKL peptide (SEQ ID NO: 8), which is directly displayed on the antigen presenting cells and not delivered to the cytoplasm of the cells first. In a preferred embodiment, the bioactive loading capacity and efficiency should lead to an absorbance of that is equal to the saturation absorbance of the SIINFEKL peptide (SEQ ID NO: 8), control using the antigen presentation assay described by Sanderson, S.; Shastri, N. in *Inter. Immun.* 1994, 6, 369-376.

A preferred basic minimal level of antigen presentation that the particles should effectuate is about 50% T-cell activation as the minimum level of T-cell activation. Efficient microgels should need approximately 500 particles per antigen presenting cell. The level beyond which the starting amount of bioactive material and particles compared to the amount of antigen presentation is inefficient and unpreferred is considered about 5 mg/ml of particles to generate a 100% T cell activation. This level is inefficient and unpreferred because of the potential toxicity involved with the delivery vehicles.

The LacZ MHC Class I antigen presentation assay, as described by the antigen Sanderson, S.; Shastri, N. in *Inter. Immun.* 1994, 6, 369-376, is performed with degradable polymer particles made according to Example 7 with the degradable polymers in Example 1 and 3 to test their ability to deliver proteins into APCs for Class I antigen presentation. This experiment uses the LacZ B3Z hybridoma, which is a CTL that recognizes the peptide sequence, SIINFEKL (SEQ ID NO: 8), from ovalbumin, complexed with the MHC Class I molecule H-2 $K^b$. This hybridoma produces P-galactosidase after encountering APCs that present SIINFEKL as a Class I antigen, thus allowing Class I antigen presentation to be quantified by measuring β-galactosidase activity.

A proper control would be to compare the amount presented by the gel particles of the invention when incubated with the SIINFEKL peptide (SEQ ID NO: 8), which is directly displayed on the antigen presenting cells and not delivered to the cytoplasm of the cells first. A maximum absorbance of 0.25 is observed with the SIINFEKL peptide (SEQ ID NO: 8), which results in 100% T-cell activation. At about 0.4 mg of particle/mL, degradable particles made as in Examples 1, should show an absorbance close to that of 0.25 at which 100% T-cell activation occurs.

The results of the Class I antigen presentation assay should show that greater T-cell activation is seen for albumin loaded particles vs. free protein. APCs incubated with free ovalbumin are not able to activate CTLs, indicating that these APCs are unable to present free ovalbumin as a Class I antigen. This is presumably because ovalbumin endocytosed by the APCs, is sequestered in lysosomes, and does not have access to the APC cytoplasm. In contrast, APCs incubated with ovalbumin encapsulated in the degradable particles, can efficiently activate CTLs. Ovalbumin encapsulated in the degradable particles is expected to be several orders of magnitude more efficient than free ovalbumin at inducing the activation of CTLs at, for example, 1 µg/ml of ovalbumin encapsulated in the degradable particles giving T cell activation levels that are expected to be 3 times greater than 1 mg/ml of free ovalbumin. For example, the U.V. absorbance resulting from activation with 1 mg/ml of free ovalbumin may be only 0.037 versus 0.1106 for activation with 1 µg/mL of ovalbumin encapsulated in the degradable particles. Thus the acid degradable particles should be capable of delivering protein antigens into APCs for Class I antigen presentation.

Higher protein loading in the degradable particles is expected to lead to an increase in antigen presentation.

EXAMPLE 9

Toxicity of Degradable Particles

The toxicity of bioactive material loaded degradable particles can be measured with the yellow tetrazolium salt, 3-(4,5-dimethylthiazolyl-2)-2,5-diphenyltetrazolium bromide (MTT), assay using RAW 309.CR1 macrophage cells (ATCC No. TIB-69, American Type Culture Collection, Manassas, Va.). The cells are incubated with the degradable particles in DMEM media with 10% F.B.S. The degradable particles are aspirated from the cells and then washed several times with PBS and allowed to grow for 24-48 hours. The cell viability is determined by measuring the absorbance of the reduced MTT reagent using the protocol described in Freshney et al. (Freshney, I. R. (1994) *Culture of animal cells*, Wiley-Liss, Inc, New York, N.Y.) as compared to a control. MTT (yellow) is reduced metabolically by healthy cells in part by the action of dehydrogenase enzymes in mitochondria, to generate purple formazan crystals, which are solubilized by the addition of a detergent and the absorbance is measured at 570 nm. Thus, the measurement of the ability of cells to reduce the MTT reagent metabolically is a measurement of the health of the cell population.

RAW 309.CR1 macrophage cells are split at $5 \times 10^4$ cells per well in a 96 well plate and allowed to grow overnight. The cells are then incubated with the degradable particles with variable amounts of loaded ovalbumin for 24 hours in DMEM media with 10% F.B.S. The degradable particles are then aspirated from the cells, and then washed several times with PBS and allowed to grow for another 24 hours.

The cell viability is determined by measuring the absorbance of the reduced MTT reagent. The MTT assay is performed using 0.5, 1, 2.5 and 5 mg particles/mL serum in each well with a particle loading of 10 micrograms protein/mg particle. After 24 hours, number of viable cells remaining is observed. It is preferred that at least 50%, more preferably 80-90% viable cells remain. Thus, it can be found whether the degradable particles of the invention are not toxic to mammalian cells if more than 50% of the cells remain viable.

particles, and about 52% viable cells remaining in the 5 mg protein/mL particles.

EXAMPLE 10

Cytoplasmic Release of Bioactive Material from Degradable Polymer Particles

Degradable particles are made according to Example 7 with the degradable polymers in Example 1 and 3, encapsulating fluorescently labeled dextran (because it easier to label and observe than fluorescence-labeled DNA) and fed to macrophage cells and compared to non-degradable control particles. When a nondegradable particle is used, the fluorescence is more localized showing that when nondegradable microgels have been taken up by the cells, they remain sequestered in the lysosome without a mechanism of release. When the acid degradable particles are used, the fluorescence is more diffuse within the cytoplasm of cells, which is indicative of cytoplasmic release of the degradable particle contents.

EXAMPLE 11

In Vivo Studies to Assess the Degradable Polymer Particle Delivery of Vaccine Therapeutics to Antigen Presenting Cells To assess the ability of the acid-degradable protein-loaded particles to deliver protein to the cytoplasm of APCs and activate CTLs and provide a protective immunity in vivo, a preliminary tumor protection experiment is performed using the EG7 tumor model (El-Shami, K., Tirosh, B., Bar-Haîm, E., Carmon, L., Vadai, E., Fridkin, M., Feldman, M., and Eisenbach, L. (1999) MHC class I-restricted epitope spreading in the context of tumor rejection following vaccination with a single immunodominant CTL epitope. *Eur. J. Immunol.* 29, 3295-3301; Kim, T. S., Chung, S. W., and Hwang, S. Y. (2000) Augmentation of antitumor immunity by genetically engineered fibroblast cells to express both B7.1 and interleukin-7. *Vaccine* 18, 2886-2894). EG7 is a derivative of the thymoma EL4, which was transfected with the ovalbumin gene, making it a target cell for CTLs activated against ovalbumin. The degradable polymer chosen for in vivo study should demonstrate good dispersibility which may be an important consideration for the study if the particles must be suspended in saline and injected into animals. Certain degradable polymers may be somewhat more difficult to suspend, most likely due to a degree of particle aggregation as a result of higher ovalbumin content.

Briefly, in an in vivo study, the degradable particles are injected into the food pad of CD4 or CD8 transgenic mice to show that the particles can activate cytotoxic T lymphocytes in vivo. More preferably, delivery is by injection of 50 µl of resuspended particle using a 25 gauge syringe in the flanks of these transgenic mice. At least 50 µg of OVA/mouse should suffice per injection with at least 3 mice per group injected. Also 150 µg of microgels with OVA and a similar amount of mirogels used for control are injected. The lymph nodes are isolated 7 days after the injection and analyzed for antigen specific T cell priming.

In Vivo Tumor Protection Experiment. Experiments are performed with female C57BL/6 mice and all immunizations were administered by subcutaneous injections using 26 gauge needles. There are three groups (15 mice per group): control mice injected with saline (200 µL); mice injected with free ovalbumin in saline (50 µg in 200 µL); and mice injected with ovalbumin encapsulated in particles dispersed in saline (1.13 mg particles, corresponds to 50 µg ovalbumin, in 200 µL). A second identical immunization is delivered 2 weeks after the first. Then 10 days after the second immunization, tumors are established by administering an injection of $1 \times 10^6$ EG7-OVA tumor cells in 100 µL saline into the shaved left flank of each mouse. One week prior to injection, the EG7 cells are stained with the anti-SIINFEKL/$K^b$ monoclonal antibody 25.D1-16 and the secondary goat anti-mouse antibody labeled with R-phycoethrin (PE). Then highly ovalbumin-expressing cells are collected using fluorescence-activated cell sorting (FACS) and proliferated. After injection, the tumor growth is monitored by measuring two perpendicular axes using digital calipers. Tumor volume is then calculated using the equation, volume=$0.5 \times \text{length} \times \text{width}^2$, with the length being the longest diameter and the width being the shortest diameter of the two perpendicular measurements. Once the tumor reaches 1.5 cm in average diameter, the mouse is removed from the experiment and euthanized according to guidelines set by the UC-Berkeley Animal Care and Use Committee. Mice are also removed if they showed other signs of pain or distress such as a lack of cleaning, eating, or mobility. A log rank test is used to determine p-values. A p-value of 0.05 or less is considered to be statistically significant.

In a previous experiment described in Standley et al., Acid-degradable particles for protein-based vaccines: enhanced survival rate for tumor-challenged mice using ovalbumin model, *Bioconjug Chem.* 2004 November-December; 15(6): 1281-8, using polyacrylamide particles made with compound 8 as a crosslinker, mice injected showed slower tumor growth and 100% survival rate after 17 days. These encouraging preliminary results suggest that main-chain degradable particles using compound 8 as a monomer can stimulate an immune response against EG7 tumor cells and provide a protective immune response against tumor cells in vivo.

Future experiments can seek to take advantage of the synthetic flexibility of the presently described delivery system through incorporation of APC targeting and immunostimulatory groups such as mannose and CpG DNA into the present main-chain degradable particles. Additional studies will also test samples with varied doses and protein loadings to determine if these variables have the same effect in vivo as they do in vitro.

EXAMPLE 12

Figure 19:
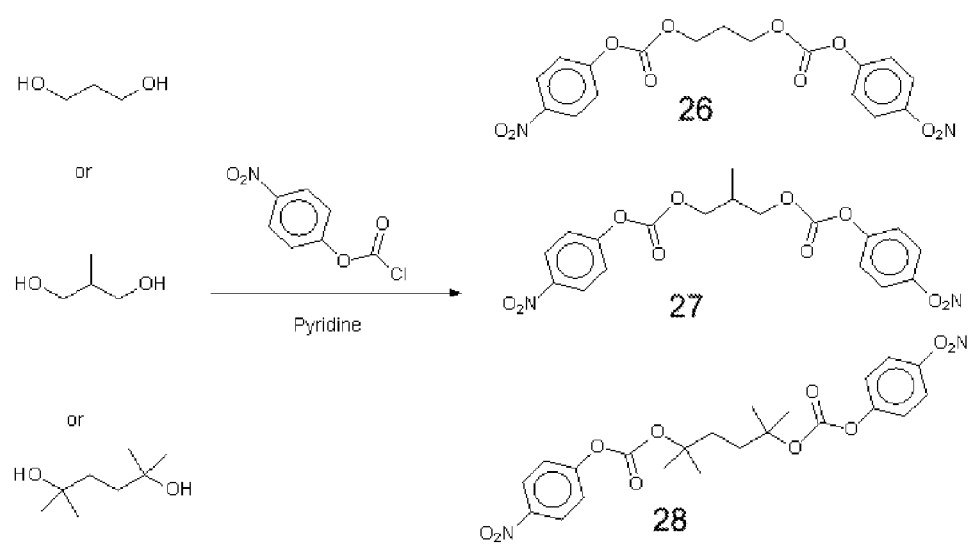
FIG. 19 shows the synthesis of one type of bis-electrophiles from typical aliphatic diols.
Figure 20:
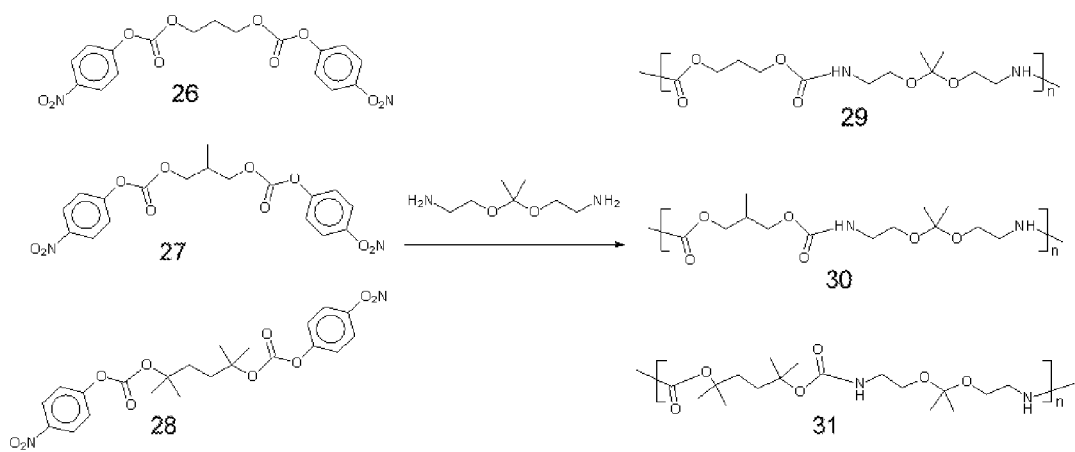
FIG. 20 shows the synthesis of acid-degradable polymers from acid degradable diamine monomer and typical bis-electrophiles.

Preparation of Activated p-Nitrophenylcarbonate Bis-Electrophiles from Aliphatic Diols Referring now to FIG. 19, aliphatic diols 1,3-propanediol, 2-methyl-1,3-propanediol, and 2.5-dimethyl-2,5-hexanediol were converted into the corresponding bis-p-nitrophenylcarbonates 26, 27, and 28, respectively, by reaction of the diols with p-nitrophenylchloroformate using a procedure analogous to that described in example 2 for the preparation of compound 14 (FIG. 10) from 1,6-hexanediol in a mixture of dichloromethane and pyridine adjusted for solubility. Following washing and drying, the crude products were purified by column chromatography and the purified bis-electrophiles (Compounds 26, 27, 28, respectively) were used directly in the preparation of the corresponding acid-degradable polymers (compounds 29, 30, 31, respectively).

EXAMPLE 13

Preparation of Acid-Degradable Polymers 29, 30 and 31

These polymers were prepared by reaction of the bis-electrophiles 26, 27, and 28, respectively with compound 10 (FIG. 9), the bis-nucleophilic amine 2,2-bis-(2-aminoethoxy) propane using procedures analogous to those described in Example 3 for the preparation of polymers 19 and 20 (compounds 19, 20, FIG. 11) with stoichiometric amounts of the bis-electrophile and acid-degradable diamine in dry dichloromethane-triethylamine; in some cases the starting monomer were not fully soluble in the small amount of solvent used but all solid material dissolved as the reaction proceeded. Following work-up, the polymers were characterized and their molecular weights evaluated by gel permeation chromatography. Typical number average molecular weights for the purified polymers were in the range $Mn$=4,000-15,000 with a polydispersity of 1.5-2.5.

EXAMPLE 14

Degradation Products of Polymers 29 and 30

The degradation reactions were carried out as described in Example 4. NMR and Mass spectrometric analysis of the mixture obtained after degradation showed that it contained the expected acetone and small molecules 32 and 33, respectively shown in FIG. 21. This finding was also confirmed by monitoring the degradation by gas chromatography.

The present examples, methods, procedures, specific compounds and molecules are meant to exemplify and illustrate the invention and should in no way be seen as limiting the scope of the invention. Any patents, publications, publicly available sequences mentioned in this specification are indicative of levels of those skilled in the art to which the invention pertains and are hereby incorporated by reference to the same extent as if each was specifically and individually incorporated by reference.

---

What is claimed is:

1. A composition comprising a main chain acid-degradable step-growth polymer containing Structure (I) in each repeating unit, wherein Structure (I) is

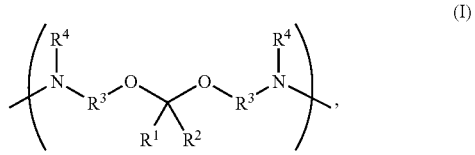

wherein $R^1$ and $R^2$ are H, $CH_3$, an alkyl, or an aryl, aryl alkyl, or substituted aryl alkyl group, wherein $R^1$ and $R^2$ are the same or different but are not simultaneously H, $R^3$ is $(CH_2)_n$, where n=2-6, or $CH_2CH(CH_3)CH_2$, and $R^4$ is H, $CH_3$, or $CH_2CH_3$.

2. The composition of claim 1, wherein $R^1$ and $R^2$ are H, or $CH_3$, $R^3$ is $CH_2CH_2$, and $R^4$ is H, $CH_3$, or $CH_2CH_3$.

3. The composition of claim 1, wherein $R^1$=H and $R^2$= —$C_6H_4$—O($CH_2CH_2O)_m$—$R^5$ wherein m=1-5 and $R^5$=$CH_3$ or $C_2$-$C_6$ alkyl.

4. The composition of claim 1, wherein the acid-degradable step-growth polymer is made by the condensation polymerization of an AA monomer and BB monomer, wherein at least one of the monomers contains Structure (I).

5. The composition of claim 4, wherein the AA monomer is a bis-nucleophile and the BB monomer is a bis-electrophile containing Structure(I), wherein the AA monomer bis-nucleophile is any of the following: any primary or secondary amine, any diol, any dithiol, or any of the following structures:

(II)

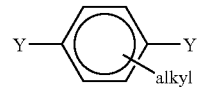

Y-alkyl-Y (III)

Y-aryl-Y (IV)

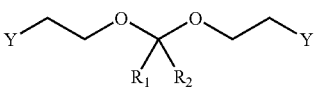

(V)

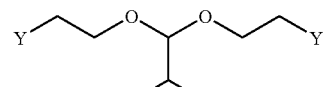

(VI)

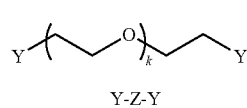

(VII)

(VIII)

Y-Z-Y (IX)

wherein Y=OH, SH, $NH_2$, or NH-alkyl, in (VII) $R^6$=—O($CH_2CH_2O)_m$—$R^5$ wherein m=1-5 and $R^5$=$CH_3$ or $C_2$-$C_6$ alkyl, in (VIII) k=1-6, and in (IX) Z is a functional group unaffected by polymerization conditions that can be further modified post polymerization.

6. The composition of claim 4, wherein the AA monomer is a primary/secondary diamine and the BB monomer contains two amine-reactive functional groups and either the AA or BB monomer contains structure (I).

7. The composition of claim 6, wherein the BB monomer has the general formula of X—R—X, wherein X is the amine-reactive functional group, wherein the BB monomers are selected from the following: diisocyanate (OCN—R—NCO), phosgene (Cl—CO—Cl), S=C=N—R—N=C=S, monomers having the following structures

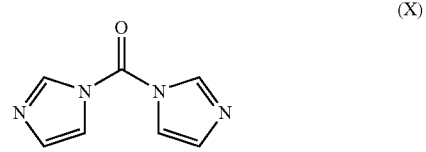

(X)

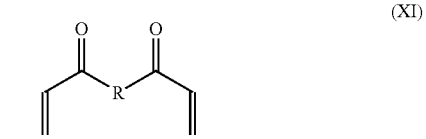

(XI)

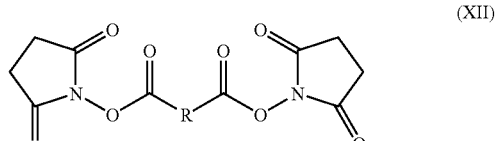

(XII)

(XIII)

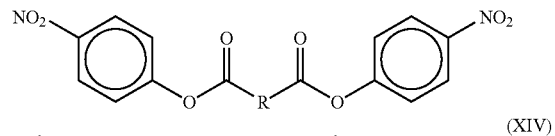

(XIV) wherein

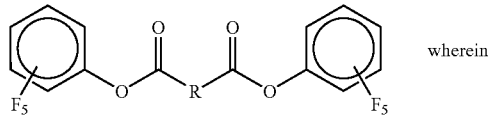

R = alkyl, aryl, arylalkyl, 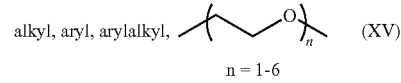 (XV)

n = 1-6

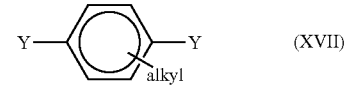 (XVII)

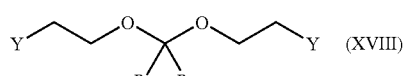 (XVIII)

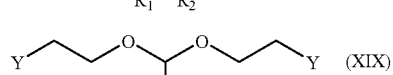 (XIX)

 (XX)

 (XXI)

Y-alkyl-Y (XXII)

Y-aryl-Y (XXIV), wherein Y=nothing or Y=O, NH, S, N-alkyl, $R^1$ and $R^2$ are H, $CH_3$, an alkyl or substituted alkyl, an aryl alkyl or a substituted aryl group, wherein $R^1$ and $R^2$ are the same or different but are not simultaneously H, in (XX) k=1-6, in (XIX) $R^6$ is $—O(CH_2CH_2O)_m—R^5$ and m=1-5 and $R^5$ is $CH_3$ or $C_2$-$C_6$ alkyl, and in (XXI) Z=a functional group unaffected by polymerization conditions that can be further modified post polymerization.

8. The composition of claim 4, wherein both the AA monomer and BB monomer contain Structure (I).

9. The composition of claim 1, wherein each repeat unit of said polymer comprises a repeat unit selected from the group consisting of:

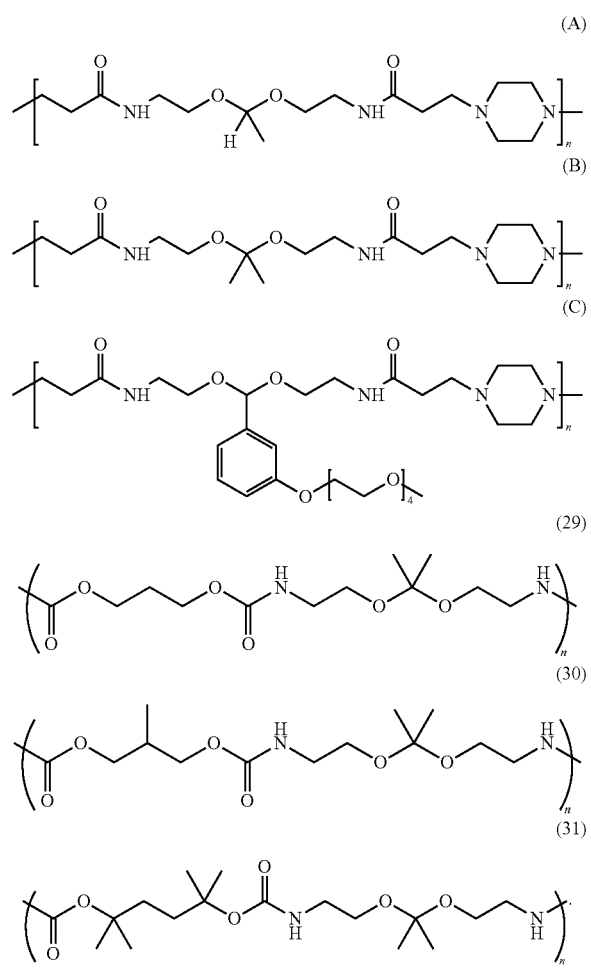

10. The composition of claim 9, wherein each repeat unit of said polymer is comprised of (30).

11. The composition of claim 7, wherein Z is an alkyl or aryl group also containing a pendant protected hydroxyl, amine or carboxyl group.

12. An acid-degradable step-growth polymer comprising an acid degradable, pH dependent backbone incorporating a group having the Structure (I) of claim 1 in each repeating unit of the polymer, whereby the group is designed to remain stable in plasma at neutral physiological pH (about 7.4), but degrade by hydrolysis in the more acidic environment of about pH 5.0-6.0, thereby resulting in main-chain degradation upon hydrolysis, and whereby the resulting degradation products are small molecules.

13. The acid-degradable step-growth polymer of claim 12 wherein the polymer is a polyamide, polyurea, polyurethane, or polyamidoamine.

14. The acid-degradable step-growth polymer of claim 12, wherein the polymer is processed to deliver a bioactive material, whereupon the bioactive material is released in response to mildly acidic conditions found in tumors, inflammatory tissues, and in cellular compartments.

15. The acid-degradable step-growth polymer of claim 14, wherein the bioactive material is selected from the group consisting of antigens, proteins, polynucleotides, polypeptides, small drug molecules and other bioactive material having a physiological effect on a cell.

16. The acid-degradable step-growth polymer of claim 14, wherein the polymer is processed to form particles for delivery to a cell.

17. The acid-degradable step-growth polymer of claim 16, wherein the particle size is 30 nm to 5000 nm.

18. The acid-degradable step-growth polymer of claim 17, wherein the particle size is 30 nm to 2000 nm.

19. The acid-degradable step-growth polymer of claim 18, wherein the particle size is 40 to 100 nm.

20. The acid-degradable step-growth polymer of claim 14, wherein the polymer is processed to form an implant device for delivery to a tissue.

21. A method of delivering a bioactive material to a cellular interior, comprising: providing to the cell degradable particles having a bioactive material bound within or conjugated to an acid-degradable step-growth polymer having Structure (I) of claim 1 in each repeating unit, whereby hydrolysis within an acidic cellular compartment cleaves the acid-degradable linkage in Structure (I) and releases said bioactive material.

22. A method of preparing a step-growth acid-degradable composition for delivering a bioactive material to a cell, comprising the steps of (a) preparing a mixture which contains an AA monomer and a BB monomer, wherein at least one of the monomers has an acid-degradable linkage; (b) polymerizing the monomers to form a polymer containing Structure (I) of claim 1 wherein each repeating unit contains the acid-degradable linkage; (c) forming particles of the polymer in the presence of a bioactive material; and (d) recovering the resulting polymer particles having bioactive material bound or entrapped thereto.

* * * * *